US009139873B2

(12) United States Patent
Wang et al.

(10) Patent No.: US 9,139,873 B2

(45) **Date of Patent: *Sep. 22, 2015**

(54) METHODS OF USING IMPROVED POLYMERASES

(71) Applicant: Bio-Rad Laboratories, Inc., Hercules, CA (US)

(72) Inventors: Yan Wang, San Francisco, CA (US); Peter Vander Horn, Foster City, CA (US); Lei Xi, Foster City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,353

(22) Filed: Jun. 21, 2013

(65) Prior Publication Data

US 2014/0220577 A1 Aug. 7, 2014

Related U.S. Application Data

(63) Continuation of application No. 13/560,075, filed on Jul. 27, 2012, now Pat. No. 8,476,045, which is a continuation of application No. 10/306,827, filed on Nov. 27, 2002, now Pat. No. 8,232,078.

(60) Provisional application No. 60/333,966, filed on Nov. 28, 2001.

(51) Int. Cl.

| | |
|---|---|
| ***C12N 9/12*** | (2006.01) |
| ***C12Q 1/68*** | (2006.01) |
| ***C07K 14/195*** | (2006.01) |
| ***C12N 15/10*** | (2006.01) |
| ***C12N 15/62*** | (2006.01) |
| ***C12P 19/34*** | (2006.01) |

(52) U.S. Cl.

CPC .............. *C12Q 1/686* (2013.01); *C07K 14/195* (2013.01); *C12N 9/1252* (2013.01); *C12N 15/10* (2013.01); *C12N 15/62* (2013.01); *C12P 19/34* (2013.01); *C12Y 207/07007* (2013.01); *C07K 2319/00* (2013.01); *C07K 2319/80* (2013.01)

(58) Field of Classification Search

None

See application file for complete search history.

(56) References Cited

U.S. PATENT DOCUMENTS

| | | | |
|---|---|---|---|
| 5,436,149 | A | 7/1995 | Barnes |
| 5,512,462 | A | 4/1996 | Cheng |
| 5,614,365 | A | 3/1997 | Tabor et al. |
| 5,658,751 | A | 8/1997 | Yue et al. |
| 5,972,603 | A | 10/1999 | Bedford et al. |
| 5,994,056 | A | 11/1999 | Higuchi |
| 6,171,785 | B1 | 1/2001 | Higuchi |
| 6,228,628 | B1 | 5/2001 | Gelfand et al. |
| 6,627,424 | B1 | 9/2003 | Wang |

FOREIGN PATENT DOCUMENTS

| | | | |
|---|---|---|---|
| CA | 2379165 | A1 | 2/2001 |
| DE | 198 40 771 | A1 | 2/2000 |
| WO | WO 01/11051 | A2 | 2/2001 |
| WO | WO 01/92501 | A1 | 12/2001 |

OTHER PUBLICATIONS

Bedford, E., et al., "The thiroedoxin binding domain of bacteriophage T7 DNA polymerase confers processivity on *Escherichia coli* DNA polymerase I," *Proc. Natl. Acad. Sci. USA* (Jan. 1997) 94: 479-484.

Consonni, et al, "A single point mutation in the extreme heat- and pressure-resistant Sso7d protein from sulfolobus solfataricus leads to a major rearrangement of the hydrophobis core", *Biochemistry* (1999) 38: 12709-12717.

Goldsby, et al., *Immunology*, Fifth Edition, section "Cross-Reactivity", p. 141, 2003.

Lim, Susan E., et al.; "The mitochondrial p55 accessory subunit of human DNA polymerase γ enhances DNA binding, promotes processive DNA synthesis, and confers *N*-ethylmaleimide resistance"; *The Journal of Biological Chemistry* (1999) 274(53): 38197-38203.

Morrison, Tom B., et al.; "Quantification of low-copy transcripts by continuous SYBR® green I monitoring during amplification"; *Biotechniques* (1998) 24: 954-962.

Motz, et al., "Elucidation of an archael replication protein network to generate enhanced PCR enzymes", *J. Biol. Chem.* (2002) 277: 16179-16188.

Pavlov, A., et al., "Helix-hairpin-helix motifs confer salt resistance and processivity on chimeric DNA polymerases," *PNAS* (2002) 99(21): 13510-13515.

Robinson, Howard, et al.; "The hyperthermophile chromosomal protein Sac7d sharply kinks DNA"; *Nature* (Mar. 12, 1998) 392: 202-205.

Shehi, et al., "Thermal stability and DNA binding activity of a variant form of Sso7d protein from the archeon sulfolobus solfataricus truncated at leucine 54", *Biochemistry* (2003) 42: 8362-8368.

Wang, Y., et al., "A novel strategy to engineer DNA polymerases for enhanced processivity and improved performance in vitro" *Nucleic Acids Research* (2004) 32(3): 1197-1207.

Weisshart, et al., "Herpes simplex virus processivity factor UL42 imparts increased DNA-binding specificity to the viral DNA polymerase and decreased dissociation from primer-template without reducing the elongation rate", *J. Virology* (1999) 73: 55-66.

*Primary Examiner* — Richard Hutson

(74) *Attorney, Agent, or Firm* — Kilpatrick Townsend & Stockton LLP

(57) ABSTRACT

This invention provides for methods of sequencing and performing polymerase reactions using an improved generation of nucleic acid polymerases. The improvement is the fusion of a sequence-non-specific nucleic-acid-binding domain to the enzyme in a manner that enhances the processivity of the polymerase.

6 Claims, 2 Drawing Sheets

METHODS OF USING IMPROVED POLYMERASES

CROSS-REFERENCES TO RELATED APPLICATIONS

This application is a continuation of U.S. application Ser. No. 13/560,075, filed Jul. 27, 2012, which is a continuation of U.S. patent application Ser. No. 10/306,827 filed Nov. 27, 2002, issued as U.S. Pat. No. 8,232,078, which claims the benefit of U.S. provisional application No. 60/333,966 filed Nov. 28, 2001. Each application is herein incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The sequence listing written in file 94260-000921US-879581.txt, created on Jun. 21, 2013, 72,307 bytes, machine format IBM-PC, MS-Windows operating system, is hereby incorporated by reference.

FIELD OF THE INVENTION

This invention provides more efficient methods of performing polymerase reactions. The methods employ an improved generation of nucleic acid polymerases. The improvement is the joining sequence-non-specific nucleic-acid-binding domain to the enzyme in a manner that enhances the ability of the enzyme to bind and catalytically modify the nucleic acid.

BACKGROUND OF THE INVENTION

The processivity of a polymerase, i.e., the amount of product generated by the enzyme per binding event, can be enhanced by increasing the stability of the modifying enzyme/nucleic acid complex. The current invention now provides enhanced polymerase assays that employ novel modifying enzymes in which the double-stranded conformation of the nucleic acid is stabilized and the processivity of the enzyme increased by joining a sequence-non-specific double-stranded nucleic acid binding domain to the enzyme, or its catalytic domain which are disclosed e.g., in co-pending U.S. application Ser. No. 09/870,353 and WO01/92501. The modifying proteins that are processive in nature exhibit increased processivity when joined to a binding domain compared to the enzyme alone.

There is a need to enhance polymerase reactions in many applications. For example, SYBR Green I (Molecular Probes, Eugene, Oreg.; U.S. Pat. Nos. 5,436,134 and 5,658,751), a fluorescent dye that is specific for dsDNA detection, is widely used in real-time PCR reactions to monitor the generation of dsDNA through each cycle of amplification. However, the addition of SYBR Green I inhibits the activity of DNA polymerases used in PCR. Similarly, it is often desirable to use PCR for the analysis of crude or "dirty" nucleic acid samples. For example, colony PCR is a useful technique in which small samples of single bacterial colonies are lysed and added directly to PCR reactions for the purpose of screening colonies for particular DNA sequences. However, colony PCR has a high failure rate, because of residual contaminants from the colony. Thus, polymerases that are resistant to such inhibitors, e.g., fluorescent dyes and impurities present in the cell extracts, are needed in order to obtain more efficient polymerase reactions, e.g., PCR.

There is also a need to improve sequencing reactions. Polymerases currently employed in sequencing reactions, e.g., cycle sequencing, are often inefficient. For example, cycle sequencing is often performed with poorly-processive enzymes. Often, the enzymes used are ΔTaq derivatives, which have Taq polymerase's 5'-3' nuclease domain removed, and have a processivity of about 2 bases. Also, in the case of dye terminator-sequencing, dITP is used in place of dGTP, which causes polymerase pausing and dissociation at G nucleotides. These enzymes therefore produce a large number of sequence products that are improperly terminated. These stops compete with, and negatively effect, the production of properly terminated sequence products. Furthermore, if a polymerase dissociates during primer extension of a template containing a repeat unit (e.g., a triplet repeat) or secondary structure (e.g., a stem and loop), the 3' end can denature and reanneal so as to prime at a different location on the template—for example, in the case of a repeat, the reannealing could occur at a different repeat; or in the case of secondary structure, improper reannealing could delete out a section of the template. Thus, dissociation of the polymerase during sequencing can cause a problem in efficiently obtaining reliable sequencing information.

The current invention addresses both of these needs, i.e., the need for enhancing polymerase reactions performed in the presence of inhibitors and the need for enhancing processivity in DNA sequencing applications). The current invention provides such enhanced, or improved, polymerase reactions. The improvement is the use of a polymerase that has increased processivity due to the presence of a sequence-non-specific nucleic-acid-binding domain that is joined to the polymerase.

BRIEF SUMMARY OF THE INVENTION

The present invention provides methods of performing more efficient polymerase reactions using a polymerase protein comprising a polymerase domain joined to a sequence-non-specific double-stranded nucleic acid binding domain. Typically the presence of the sequence non-specific double-stranded nucleic acid binding domain enhances the processivity of the polymerase compared to an identical protein not having a sequence-non-specific nucleic acid binding domain joined thereto.

The polymerase domain can be thermally stable, e.g., a *Thermus* polymerase domain such as a ΔTaq polymerase domain, or a *Pyrococcus* polymerase domain.

In one embodiment the sequence-non-specific nucleic-acid-binding domain specifically binds to polyclonal antibodies generated against either Sac7d or Sso7d. Alternatively, the sequence-non-specific nucleic-acid-binding domain contains a 50 amino acid subsequence containing 50% amino acid similarity to Sso7d. Typically, the sequence-non-specific nucleic-acid-binding domain is Sso7d or specifically binds to polyclonal antibodies generated against Sso7d.

The polymerase reaction can be performed on a target nucleic acid that is present in a crude preparation of a sample. In another embodiment, the polymerase reaction is performed in the presence of a molecule that typically inhibits polymerases, e.g. fluorescent dyes such as SYBR Green I. Further, the polymerase may be used in cycle sequencing reactions to obtain longer sequences, e.g., through regions of secondary structure that prevent sequencing using unmodified polymerases.

DETAILED DESCRIPTION OF THE INVENTION

Definitions

Figure 1A:
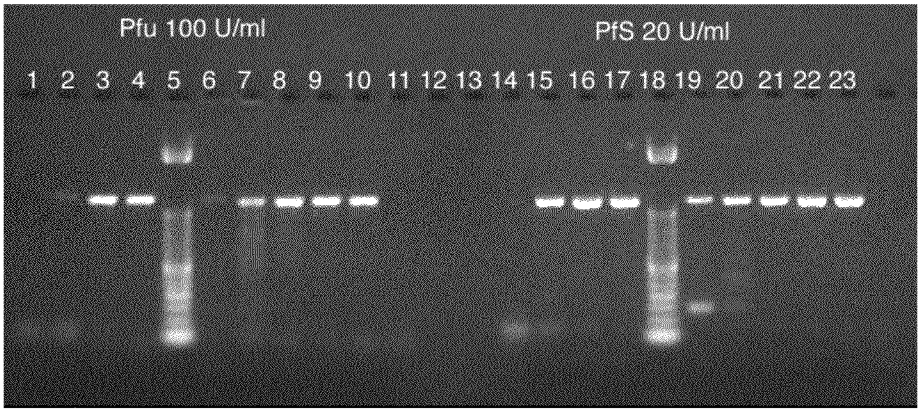
FIGS. 1A and 1B show the results of a PCR reaction performed in the presence of contaminants using an improved polymerase.

"Archaeal small basic DNA-binding protein" refers to protein of between 50-75 amino acids having either 50% homology to a natural Archaeal small basic DNA-binding protein such as Sso-7d from *Sulfolobus sulfataricus* or binds to antibodies generated against a native Archaeal small basic DNA-binding protein.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Efficiency" in the context of a nucleic acid modifying enzyme of this invention refers to the ability of the enzyme to perform its catalytic function under specific reaction conditions. Typically, "efficiency" as defined herein is indicated by the amount of product generated under given reaction conditions.

"Enhances" in the context of an enzyme refers to improving the activity of the enzyme, i.e., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Nucleic-acid-modifying enzyme" refers to an enzyme that covalently alters a nucleic acid.

"Polymerase" refers to an enzyme that performs template-directed synthesis of polynucleotides. The term, as used herein, also refers to a domain of the polymerase that has catalytic activity.

"Error-correcting activity" of a polymerase or polymerase domain refers to the 3' to 5' exonuclease proofreading activity of a template-specific nucleic acid polymerase whereby nucleotides that do not form Watson-Crick base pairs with the template are removed from the 3' end of an oligonucleotide, i.e., a strand being synthesized from a template, in a sequential manner. Examples of polymerases that have error-correcting activity include polymerases from *Pryococcus furiosus, Thermococcus litoralis*, and *Thermotoga maritima.*

Processivity refers to the ability of a nucleic acid modifying enzyme to remain bound to the template or substrate and perform multiple modification reactions. Processivity is measured by the number of catalytic events that take place per binding event.

"Sequence-non-specific nucleic-acid-binding domain" refers to a protein domain which binds with significant affinity to a nucleic acid, for which there is no known nucleic acid which binds to the protein domain with more than 100-fold more affinity than another nucleic acid with the same nucleotide composition but a different nucleotide sequence.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus, Thermus brockianus*, and *Thermus thermophilus*; any recombinant enzymes deriving from *Thermus* species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase reaction (see U.S. Pat. Nos. 4,683,195 and 4,683,202; *PCR Protocols: A Guide to Methods and Applications* (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and *PCR Protocols: A Guide to Methods and Applications*, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

"Long PCR" refers to the amplification of a DNA fragment of 5 kb or longer in length. Long PCR is typically performed using specially-adapted polymerases or polymerase mixtures (see, e.g., U.S. Pat. Nos. 5,436,149 and 5,512,462) that are distinct from the polymerases conventionally used to amplify shorter products.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A temperature profile refers to the temperature and lengths of time of the denaturation, annealing and/or extension steps of a PCR or cycle sequencing reaction. A temperature profile for a PCR or cycle sequencing reaction typically consists of 10 to 60 repetitions of similar or identical shorter temperature profiles; each of these shorter profiles may typically define a two step or three-step cycle. Selection of a temperature profile is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

PCR "sensitivity" refers to the ability to amplify a target nucleic acid that is present in low copy number. "Low copy number" refers to $10^5$, often $10^4$, $10^3$, $10^2$, or fewer, copies of the target sequence in the nucleic acid sample to be amplified.

A "template" refers to a double stranded polynucleotide sequence that comprises the polynucleotide to be amplified, flanked by primer hybridization sites. Thus, a "target template" comprises the target polynucleotide sequence flanked by hybridization sites for a 5' primer and a 3' primer.

An "improved polymerase" includes a sequence-non-specific double-stranded DNA binding domain joined to the polymerase or polymerase domain. An "unimproved polymerase" is a polymerase that does not have a sequence-non-specific double-stranded DNA binding domain.

Introduction

The current invention provides methods of performing polymerase reactions using improved polymerases. These polymerase reactions are typically more efficient and yield more product than traditional polymerases. These improved polymerases contain a polymerase domain with a binding domain joined to it. While the prior art taught that nucleic acid binding proteins can increase the binding affinity of enzymes to nucleic acid, the group of binding proteins having the ability to enhance the processive nature of the enzymes is of particular value. Not to be bound by theory, binding domains of the invention typically dissociate from double-stranded nucleic acid at a very slow rate. Thus, they increase the processivity and/or efficiency of a modifying enzyme to which they are joined by stabilizing the enzyme-nucleic acid complex. Accordingly, this invention results from the discovery that DNA-binding domains can stabilize the double-stranded conformation of a nucleic acid and increase the efficiency of a catalytic domain that requires a double-stranded substrate. Described herein are examples and simple assays to readily determine the improvement to the catalytic and/or processive nature of catalytic nucleic acid modifying enzymes, e.g., polymerases.

Polymerase Domains.

DNA polymerases are well-known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Similarly, RNA polymerases typically include eukaryotic RNA polymerases I, II, and III, and bacterial RNA polymerases as well as phage and viral polymerases. RNA polymerases can be DNA-dependent and RNA-dependent.

In one embodiment, polymerase domains that have an error-correcting activity are used as the catalytic domain of the improved polymerases described herein. These polymerases can be used to obtain long, i.e., 5 kb, often 10 kb, or greater in length, PCR products. "Long PCR" using these improved polymerases can be performed using extension times that are reduced compared to prior art "long PCR" polymerase and/or polymerase mixtures. Extension times of less than 30 seconds per kb, often 15 seconds per kb, can be used to amplify long products in PCR reactions using the improved polymerases. Furthermore, these modified polymerases also exhibit increased sensitivity.

Prior-art non-error-correcting polymerases such as Taq polymerase are capable of amplifying DNA from very small input copy concentrations, such as, in the extreme, 10 copies per ml. However, because of the low fidelity of such polymerases, products cloned from such amplifications are likely to contain introduced mutations.

Prior-art error-correcting polymerases such as Pfu copy DNA with higher fidelity than Taq, but are not capable of amplifying DNA from small input copy concentrations. The hybrid error-correcting polymerases of the invention exhibit much higher processivity while retaining error-correcting activity and thereby provide both sensitivity and fidelity in amplification reactions.

The activity of a polymerase can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a polymerase containing a sequence-non-specific double-stranded DNA binding domain can then be compared to the amount of product obtained with the normal polymerase enzyme, which will be described in more detail below and in the Examples.

A polymerase domain suitable for use in the invention can be the enzyme itself or the catalytic domain, e.g., Taq polymerase or a domain of Taq with polymerase activity. The catalytic domain may include additional amino acids and/or may be a variant that contains amino acid substitutions, deletions or additions, but still retains enzymatic activity.

Sequence-Non-Specific Nucleic-Acid-Binding Domain

A double-stranded sequence-non-specific nucleic acid binding domain is a protein or defined region of a protein that binds to double-stranded nucleic acid in a sequence-independent manner, i.e., binding does not exhibit a gross preference for a particular sequence. Typically, double-stranded nucleic acid binding proteins exhibit a 10-fold or higher affinity for double-stranded versus single-stranded nucleic acids. The double-stranded nucleic acid binding proteins in particular embodiments of the invention are preferably thermostable. Examples of such proteins include, but are not limited to, the Archaeal small basic DNA binding proteins Sac7d and Sso7d (see, e.g., Choli et al., *Biochimica* et *Biophysica Acta* 950: 193-203, 1988; Baumann et al., *Structural Biol.* 1:808-819, 1994; and Gao et al, *Nature Struc. Biol.* 5:782-786, 1998), Archael HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell:* 99, 155-166, 1999; De Felice et al., *J. Molec. Biol.* 291, 47-57, 1999; and Zhang et al., *Biochemistry* 34:10703-10712, 1995).

Sso7d and Sac7d

Sso7d and Sac7d are small (about 7,000 kd MW), basic chromosomal proteins from the hyperthermophilic archaeabacteria *Sulfolobus solfataricus* and *S. acidocaldarius*, respectively. These proteins are lysine-rich and have high thermal, acid and chemical stability. They bind DNA in a sequence-independent manner and when bound, increase the $T_M$ of DNA by up to 40° C. under some conditions (McAfee et al., *Biochemistry* 34:10063-10077, 1995). These proteins and their homologs are typically believed to be involved in packaging genomic DNA and stabilizing genomic DNA at elevated temperatures.

HMf-Like Proteins

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

PCNA Homologs

Many but not all family B DNA polymerases interact with accessory proteins to achieve highly processive DNA synthesis. A particularly important class of accessory proteins is referred to as the sliding clamp. Several characterized sliding clamps exist as trimers in solution, and can form a ring-like structure with a central passage capable of accommodating double-stranded DNA. The sliding clamp forms specific interactions with the amino acids located at the C terminus of particular DNA polymerases, and tethers those polymerases to the DNA template during replication. The sliding clamp in eukarya is referred to as the proliferating cell nuclear antigen (PCNA), while similar proteins in other domains are often referred to as PCNA homologs. These homologs have marked structural similarity but limited sequence similarity.

Recently, PCNA homologs have been identified from thermophilic Archaea (e.g., *Sulfalobus sofataricus, Pyroccocus furiosus*, etc.). Some family B polymerases in Archaea have a C terminus containing a consensus PCNA-interacting amino acid sequence and are capable of using a PCNA homolog as a processivity factor (see, e.g., Cann et al., *J. Bacteriol.* 181: 6591-6599, 1999 and De Felice et al., *J. Mol. Biol.* 291:47-57, 1999). These PCNA homologs are useful sequence-non-specific double-stranded DNA binding domains for the invention. For example, a consensus PCNA-interacting sequence can be joined to a polymerase that does not naturally interact with a PCNA homolog, thereby allowing a PCNA homolog to serve as a processivity factor for the polymerase. By way of illustration, the PCNA-interacting sequence from *Pyrococcus furiosus* PolII (a heterodimeric DNA polymerase containing two family B-like polypeptides) can be covalently joined to *Pyrococcus furiosus* PolI (a monomeric family B polymerase that does not normally interact with a PCNA homolog). The resulting fusion protein can then be allowed to associate non-covalently with the *Pyrococcus furiosus* PCNA homolog to generate a novel heterologous protein with increased processivity relative to the unmodified *Pyrococcus furiosus* PolI.

Other Sequence-Nonspecific Double-Stranded Nucleic Acid Binding Domains

Additional nucleic acid binding domains suitable for use in the invention can be identified by homology with known sequence non-specific double-stranded DNA binding proteins and/or by antibody crossreactivity, or may be found by means of a biochemical assay. These methods are described, e.g., in WO01/92501. Further, methods of joining the polymerase to the sequence non-specific double-stranded DNA binding protein and methods of expressing recombinant polymerases and polymerase fusion proteins are also described (see, e.g., WO01/92501).

Assays to Determine Improved Activity of Polymerase Domains.

Activity of the polymerase domain can be measured using a variety of assays that can be used to compare processivity or modification activity of a modifying protein domain joined to a binding domain compared to the protein by itself. Improvement in activity includes both increased processivity and increased efficiency.

Polymerase processivity can be measured in variety of methods known to those of ordinary skill in the art. Polymerase processivity is generally defined as the number of nucleotides incorporated during a single binding event of a modifying enzyme to a primed template.

For example, a 5' FAM-labeled primer is annealed to circular or linearized ssM13mp18 DNA to form a primed template. In measuring processivity, the primed template usually is present in significant molar excess to the enzyme or catalytic domain to be assayed so that the chance of any primed template being extended more than once by the polymerase is minimized. The primed template is therefore mixed with the polymerase catalytic domain to be assayed at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, i.e., a protein that contains a sequence non-specific double-stranded nucleic acid binding domain fused to the catalytic domain of a processive nucleic acid modifying enzyme such as a polymerase, is then compared to the processivity of the enzyme without the binding domain.

Enhanced efficiency can also be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase such as a Taq polymerase to produce more product in a PCR reaction using the 12 nucleotide primer annealed at 50° C. when it is joined to a sequence-non-specific double-stranded nucleic-acid-binding domain of the invention, e.g., Sso7d, than Taq polymerase does alone. In contrast, a binding tract that is a series of charged residues, e.g. lysines, does not enhance processivity when joined to a polymerase.

Assays such as salt sensitivity can also be used to demonstrate improvement in efficiency of a processive nucleic acid modifying enzyme of the invention. A modifying enzyme, or the catalytic domain, when fused to a sequence non-specific double-stranded nucleic acid binding domain of the invention exhibits increased tolerance to high salt concentrations, i.e., a processive enzyme with increased processivity can produce more product in higher salt concentrations. For example, a PCR analysis can be performed to determine the amount of product obtained in a reaction using a fusion Taq polymerase (e.g., Sso7d fused to Taq polymerase) compared to Taq polymerase in reaction conditions with high salt, e.g., 80 mM.

Other methods of assessing enhanced efficiency of the improved polymerases of the invention can be determined by those of ordinary skill in the art using standard assays of the enzymatic activity of a given modification enzyme.

Uses of Improved Polymerases

The invention provides improved methods of performing polymerase reactions. In one embodiment, the invention provides a method of performing a polymerase reaction in the presence of a fluorescent dye. A number of fluorescent dyes that are commonly used in reactions such as real-time PCR, have an inhibitory activity on polymerases have been typically used in PCR, e.g., Taq polymerase. For example, SYBR Green I (Molecular Probes, Eugene, Oreg.; U.S. Pat. Nos. 5,436,134 and 5,658,751), is a fluorescent dye that is specific for dsDNA detection, and is widely used in real-time PCR reactions to monitor the generation of dsDNA through each cycle of amplification. Use of dyes to monitor amplification is described in U.S. Pat. Nos. 5,994,056 and 6,171,785 and use of SYBR Green I for this purpose is described in Morrison et al., *Biotechniques* 24:954-962 (1998).

It has been observed that the addition of SYBR Green I inhibits the activity of DNA polymerases used in PCR, possibly through interfering with the binding of the polymerase to the primer-template. Additives such as DMSO are therefore often required to reduce the inhibitory effect of the dye. However, DMSO can reduce the storage stability of the enzyme and can inhibit polymerases. The current invention provides a method of performing polymerase reactions in the presence of a fluorescent dye that uses the improved polymerases described herein, which are not as sensitive to the fluorescent dye, i.e., are not inhibited to the same extent, as an unimproved polymerase.

The ability of a polymerase to perform in the presence of a dye that exhibits altered fluorescence emissions when bound to double-stranded DNA can be measured using well known polymerase assays, such as those described herein. Typically, a fluorescent dye reduces the activity of an unimproved polymerase by 25%, often 50%, 75%, or more. Polymerase activity can be assayed using the methods described herein.

The ability of an improved polymerase to perform a PCR reaction in the presence of a fluorescent dye, e.g., SYBR Green I, can also be compared to the ability of the unimproved polymerase to perform in an otherwise identical PCR reaction. The comparison can be made using a values such as the cycle threshold ($C_t$) value, which represents the number of cycles required to generate a detectable amount of DNA. An efficient polymerase may be able to produce a detectable amount of DNA in a smaller number of cycles by more closely approaching the theoretical maximum amplification efficiency of PCR. Accordingly, a lower $C_t$ value reflects a greater amplification efficiency for the enzyme. The improved enzymes exhibit 2×, often 5×, or greater activity in the presence of a fluorescent dye when compared to the unimproved enzyme.

In typical embodiments, the polymerase reaction is performed in the presence of a fluorescent dye such as SYBR Green I or Pico Green I (Molecular Probes, Eugene, Oreg.;). These dyes are unsymmetrical cyanine dyes containing a defined substituent on the pyridinium or quinolinium ring system or a substituent immediately adjacent to the nitrogen atom of the pyridinium or quinolinium ring. These and other members of the same class of dyes are described, e.g., in U.S. Pat. Nos. 5,436,134 and 5,658,751. SYBR Green I, for example, binds specifically to dsDNA with a dissociation constant in the sub-micromolar range. Upon binding, it has a large increase in its quantum yield and therefore a large increase in fluorescence.

In other embodiments, the polymerase reactions of the invention can be performed in the presence of other fluorescent compounds that typically inhibit polymerases, such as other fluorescent dyes, e.g., propidium iodide, ethidium bromide, acridines, proflavine, acridine orange, acriflavine, fluorcoumanin, ellipticine, daunomycin, chloroquine, distamycin D, chromomycin, mithramycin, ruthenium polypyridyls, and anthramycin, which also exhibit altered fluorescence emissions when bound to double-stranded DNA. Improved polymerases can be tested for resistance to other dyes using methodology well known in the arts and described herein (see, e.g., Example 6).

In another embodiment, the invention provides method of performing a polymerase reaction, e.g., a PCR reaction, in the presence of contaminants such as those present when using a crude nucleic acid sample. Inhibitors of polymerase activity are often present in crude nucleic acid sample preparations, thus presenting difficulties in using such preparations in polymerase reactions such as PCR or nucleic acid sequence. The improved enzymes are more tolerant to such contaminants. Accordingly, the improved enzymes offer advantages over standard enzymes when performing polymerase reactions, e.g. PCR, using crude nucleic acid preparations. These preparations can be from a variety of sources, including cells such as bacterial cells, plant cells, and various other cell types.

A crude nucleic acid sample typically includes contaminants that originate from the nucleic acid source or from a previous chemical or molecular biological manipulation. The improved polymerases are less sensitive to the presence of such contaminants. As noted above, polymerase activity assays can be performed using methods described herein. An improved polymerase typically exhibits 2×, 5×, 10×, or greater activity relative to the unimproved polymerase when assayed in the presence of contaminants in an otherwise identical polymerase activity assay or PCR. An exemplary analysis of polymerase activity in crude preparations is provided in Example 7. Crude preparations typically are not processed through repeated rounds of purification and are typically less than 98% pure, often less than 95% pure.

The modified polymerase enzymes are also more resistant to common additives for troublesome PCR reactions such as Betaine, DMSO, as well as resistant to salt, e.g., KCl, etc. The improved polymerase typically exhibits 2×, 5×, 10× or greater activity relative to the unimproved polymerase in the presence of such agents.

Improved polymerases can also be used in nucleic acid sequencing reactions. These reactions are well known to those of skill in the art (see, e.g., Sambrook and Russell, *Molecular Cloning, A Laboratory Manual* 3rd. 2001, Cold Spring Harbor Laboratory Press).

Improved polymerases are particular advantageous when used in sequencing reactions, in particular sequencing reactions that use thermostable polymerases, such as cycle sequencing reactions. Cycle sequencing refers to a linear amplification DNA sequencing technique in which a single primer is used to generate labeled terminated fragments by the Sanger dideoxy chain termination method. Thermostable polymerase enzymes are employed in such reactions.

Thermostable polymerases such as Taq or Pfu catalyze the incorporation of ddNTPs at a rate that is at least two orders of magnitude slower than the rate of incorporation of dNTPs. In addition, the efficiency of incorporation of a ddNTP at a particular site is affected by the local sequence of the template DNA. Modified version of polymerases that lack 5' to 3' exonuclease activity and catalyze incorporation of ddNTPs with high efficiency have been developed; however, their processivity is often poor. For example, thermostable enzymes are such as ΔTaq derivatives, which have Taq polymerase's 5'-3' nuclease domain removed, have a processivity of about 2 bases. Also, in the case of dye terminator-sequencing, dITP is used in place of dGTP, which causes polymerase pausing and dissociation at G nucleotides. These enzymes therefore produce a large number of sequence products that are improperly terminated. Furthermore, if a polymerase dissociates during primer extension of a template containing a repeat unit (e.g., a triplet repeat) or secondary structure (e.g., a stem and loop) such that the strand is not completed during a particular PCR cycle, the 3' end can denature and reanneal during a subsequent PCR cycle so as to prime at a different location on the template—for example, in the case of a repeat, the reannealing could occur at a different repeat; or in the case of secondary structure, improper reannealing could delete out a section of the template. Thus, dissociation of the polymerase is also a problem.

The use of improved polymerases as described herein can provide enhanced sequencing reactions, e.g., cycle sequencing reactions, in which there are fewer improper terminations and fewer dissociation events. This provides longer sequence reads, i.e., the number of nucleotides for which the sequence can be determined, that contain fewer ambiguities compared to reaction performed with unimproved enzymes.

The polymerases are typically modified to substitute a Y residue for an F residue (U.S. Pat. No. 5,614,365).

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of non-critical parameters that could be changed or modified to yield essentially similar results.

Example 1

Construction of Fusion Proteins

Construction of Sso7d-ΔTaq Fusion.

The following example illustrates the construction of a polymerase protein possessing enhanced processivity, in which the sequence-non-specific double-stranded nucleic acid binding protein Sso7d is fused to the *Thermus aquaticus* PolI DNA polymerase (a family A polymerase known as Taq DNA polymerase) that is deleted at the N terminus by 289 amino acids (ΔTaq).

Based on the published amino acid sequence of Sso7d, seven oligonucleotides were used in constructing a synthetic gene encoding Sso7d. The oligonucleotides were annealed and ligated using T4 DNA ligase. The final ligated product was used as the template in a PCR reaction using two terminal oligonucleotides as primers to amplify the full-length gene. By design, the resulting PCR fragment contains a unique EcoRI site at the 5' terminus, and a unique BstXI site at the 3' terminus. In addition to encoding the Sso7d protein, the above PCR fragment also encodes a peptide linker with the amino acid sequence of Gly-Gly-Val-Thr (SEQ ID NO:34) positioned at the C terminus of the Sso7d protein. The synthetic gene of Sso7d has the DNA sequence shown in SEQ ID NO:1, and it encodes a polypeptide with the amino acid sequence shown in SEQ ID NO:2.

The synthetic gene encoding Sso7d was then used to generate a fusion protein in which Sso7d replaces the first 289 amino acid of Taq. The fragment encoding Sso7d was subcloned into a plasmid encoding Taq polymerase to generate the fusion protein, as follows. Briefly, the DNA fragment containing the synthetic Sso7d gene was digested with restriction endonucleases EcoRI and BstXI, and ligated into the corresponding sites of a plasmid encoding Taq. As the result, the region that encodes the first 289 amino acid of Taq is replaced by the synthetic gene of Sso7d. This plasmid (pYW1) allows the expression of a single polypeptide containing Sso7d fused to the N terminus of ΔTaq via a synthetic linker composed of Gly-Gly-Val-Thr (SEQ ID NO:34). The DNA sequence encoding the fusion protein (Sso7d-ΔTaq) and the amino acid sequence of the protein are shown in SEQ ID NOs:3 and 4, respectively.

Construction of Sso7d-Taq Fusion.

An Sso7d/full-length Taq fusion protein was also constructed. Briefly, a 1 kb PCR fragment encoding the first 336 amino acids of Taq polymerase was generated using two primers. The 5' primer introduces a SpeI site into the 5' terminus of the PCR fragment, and the 3' primer hybridizes to nucleotides 1008-1026 of the Taq gene. The fragment was digested with SpeI and BstXI, releasing a 0.9 kb fragment encoding the first 289 amino acids of Taq polymerase. The 0.9 kb fragment was ligated into plasmid pYW1 at the SpeI (located in the region encoding the linker) and BstXI sites. The resulting plasmid (pYW2) allows the expression of a single polypeptide containing the Sso7d protein fused to the N terminus of the full length Taq DNA polymerase via a linker composed of Gly-Gly-Val-Thr (SEQ ID NO:34), the same as in Sso7d-ΔTaq. The DNA sequence encoding the Sso7d-Taq fusion protein and the amino acid sequence of the protein are shown in SEQ ID. NOS:5 and 6, respectively.

Construction of Pfu-Sso7d Fusion.

A third fusion protein was created, joining Sso7d to the C terminus of *Pyrococcus furiosus* DNA polI (a family B DNA polymerase known as Pfu). A pET-based plasmid carrying the Pfu DNA polymerase gene was modified so that a unique KpnI site and a unique SpeI site are introduced at the 3' end of the Pfu gene before the stop codon. The resulting plasmid (pPFKS) expresses a Pfu polymerase with three additional amino acids (Gly-Thr-His) at its C terminus.

Two primers were used to PCR amplify the synthetic Sso7d gene described above to introduce a Kpn I site and a NheI site flanking the Sso7d gene. The 5' primer also introduced six additional amino acids (Gly-Thr-Gly-Gly-Gly-Gly; SEQ ID NO:35), which serve as a linker, at the N terminus of the Sso7d protein. Upon digestion with KpnI and NheI, the PCR fragment was ligated into pPFKS at the corresponding sites. The resulting plasmid (pPFS) allows the expression of a single polypeptide containing Sso7d protein fused to the C terminus of the Pfu polymerase via a peptide linker (Gly-Thr-Gly-Gly-Gly-Gly; SEQ ID NO:35). The DNA sequence encoding the fusion protein (Pfu-Sso7d) and the amino acid sequence of the fusion protein are shown in SEQ ID. NOS:7 and 8, respectively.

Construction of Sac7d-ΔTaq Fusion.

A fourth fusion protein was constructed, which joined a sequence-non-specific DNA binding protein from a different species to ΔTaq. Two primers were used to PCR amplify the Sac7d gene from genomic DNA of *Sulfolobus acidocaldarius*. The primers introduced a unique EcoRI site and a unique SpeI site to the PCR fragment at the 5' and 3' termini, respectively. Upon restriction digestion with EcoRI and SpeI, the PCR fragment was ligated into pYW1 (described above) at the corresponding sites. The resulting plasmid expresses a single polypeptide containing the Sac7d protein fused to the N terminus of ΔTaq via the same linker as used in Sso7d-ΔTaq. The DNA sequence of the fusion protein (Sac7d-ΔTaq) and the amino acid sequence of the protein are shown in SEQ ID. NOs: 9 and 10, respectively.

Construction of PL-ΔTaq Fusion.

A fifth fusion protein joins a peptide composed of 14 lysines and 2 arginines to the N terminus of ΔTaq. To generate the polylysine (PL)-ΔTaq fusion protein, two 67 nt oligonucleotides were annealed to form a duplexed DNA fragment with a 5' protruding end compatible with an EcoRI site, and a 3' protruding end compatible with an SpeI site. The DNA fragment encodes a lysine-rich peptide of the following composition: NSKKKKKKKRKKRKKKGGGVT (SEQ ID NO:36). The numbers of lysines and arginines in this peptide are identical to those in Sso7d. This DNA fragment was ligated into pYW1, predigested with EcoRI and SpeI, to replace the region encoding Sso7d. The resulting plasmid (pLST) expresses a single polypeptide containing the lysine-rich peptide fused to the N terminus of ΔTaq. The DNA sequence encoding the fusion protein (PL-ΔTaq) and the amino acid sequence of the protein are shown in SEQ ID. NOS:11 and 12, respectively.

Example 2

Assessing the Processivity of the Fusion Polymerases

This example illustrates enhancement of processivity of the fusion proteins of the invention generated in Example 1.

Polymerase Unit Definition Assay

The following assay was used to define a polymerase unit. An oligonucleotide was pre-annealed to ssM13 mp18 DNA in the presence of $Mg^{++}$-free reaction buffer and dNTPs. The DNA polymerase of interest was added to the primed DNA mixture. $MgCl_2$ was added to initiate DNA synthesis at 72° C. Samples were taken at various time points and added to TE buffer containing PicoGreen (Molecular Probes, Eugene Oreg.). The amount of DNA synthesized was quantified using a fluorescence plate reader. The unit activity of the DNA polymerase of interest was determined by comparing its initial rate with that of a control DNA polymerase (e.g., a commercial polymerase of known unit concentration).

Processivity Assay

Processivity was measured by determining the number of nucleotides incorporated during a single binding event of the polymerase to a primed template.

Briefly, 40 nM of a 5' FAM-labeled primer (34 nt long) was annealed to 80 nM of circular or linearized ssM13mp18 DNA to form the primed template. The primed template was mixed with the DNA polymerase of interest at a molar ratio of approximately 4000:1 (primed DNA:DNA polymerase) in the presence of standard PCR buffer (free of $Mg^{++}$) and 200 μM of each dNTPs. $MgCl_2$ was added to a final concentration of 2 mM to initiate DNA synthesis. At various times after initiation, samples were quenched with sequencing loading dye containing 99% formamide, and analyzed on a sequencing gel. The median product length, which is defined as the product length above or below which there are equal amounts of products, was determined based on integration of all detectable product peaks. At a polymerase concentration for which the median product length change with time or polymerase concentration, the length corresponds to the processivity of the enzyme. The ranges presented in Table 1 represent the range of values obtained in several repeats of the assay.

TABLE 1

Comparison of processivity

| DNA polymerase | Median product length (nt) |
|---|---|
| ΔTaq | 2-6 |
| Sso7d-ΔTaq | 39-58 |
| PL-ΔTaq | 2-6 |
| Taq | 15-20 |
| Sso7d-Taq | 130-160 |
| Pfu | 2-3 |
| Pfu-Sso7d | 35-39 |

In comparing the processivity of modified enzyme to the unmodified enzyme, ΔTaq had a processivity of 2-6 nucleotides, whereas Sso7d-ΔTaq fusion exhibited a processivity of 39-58 nucleotides (Table I). Full length Taq had a processivity of 15-20 nucleotides, which was significantly lower than that of Sso7d-Taq fusion with a processivity of 130-160 nucleotides. These results demonstrate that Sso7d joined to Taq polymerase enhanced the processivity of the polymerase.

Pfu belongs to family B of polymerases. Unlike Taq polymerase, Pfu possesses a 3' to 5' exonuclease activity, allowing it to maintain high fidelity during DNA synthesis. A modified Pfu polymerase, in which Sso7d is fused to the C terminus of the full length Pfu polymerase, and an unmodified Pfu polymerase were analyzed in the processivity assay described above. As shown in Table I, the Pfu polymerase exhibited a processivity of 2-3 nt, whereas the Pfu-Sso7d fusion protein had a processivity of 35-39 nt. Thus, the fusion of Sso7d to the C terminus of Pfu resulted in a >10-fold enhancement of the processivity over the unmodified enzyme.

Example 3

Effect of Fusion Proteins on Oligonucleotide Annealing Temperature

This experiment demonstrates the increased efficiency of the Sso7d-ΔTaq fusion protein, compared to Taq, to produce product at higher annealing temperatures by stabilizing dsDNA.

Two primers, primer 1008 (19mer; $T_M$=56.4° C.) and 2180R (20mer; $T_M$=56.9° C.), were used to amplify a 1 kb fragment (1008-2180) of the Taq pol gene. A gradient thermal cycler (MJ Research, Waltham Mass.) was used to vary the annealing temperature from 50° C. to 72° C. in a PCR cycling program. The amounts of PCR products generated using identical number of units of Sso7d-ΔTaq and Taq were quantified and compared. The results are shown in Table 2. The Sso7d-ΔTaq fusion protein exhibited significantly higher efficiency than full length Taq at higher annealing temperatures. Thus, the presence of Sso7d in cis increases the melting temperature of the primer on the template.

The annealing temperature assay above was used to investigate whether PL-ΔTaq has any effect on the annealing temperature of primer during PCR amplification. As shown in Table 2 little or no amplified product was observed when the annealing temperature was at or above 63° C.

TABLE 2

Comparison of activities at different annealing temperatures.

| Polymerase | Activity at 63° C. | Activity at 66° C. | Activity at 69° C. |
|---|---|---|---|
| Taq | 85% | 30% | <10% |
| Sso7d-ΔTaq | >95% | 70% | 40% |
| PL-ΔTaq | <5% | nd | nd |

nd: not detectable.

Example 4

Effect of Fusion Proteins on Required Primer Length

An enhancement of $T_M$ of the primers (as shown above) predicts that shorter primers could be used by Sso7d-ΔTaq, but not by Taq, to achieve efficient PCR amplification. This analysis shows that Sso7d-ΔTaq is more efficient in an assay using shorter primers compared to Taq.

Primers of different lengths were used to compare the efficiencies of PCR amplification by Sso7d-ΔTaq and by Taq. The results are shown in Table 3. When two long primers, 57F (22mer, $T_M$=58° C.) and 732R (24mer, $T_M$=57° C.) were used, no significant difference was observed between Sso7d-ΔTaq and Taq at either low or high annealing temperatures. When medium length primers, 57F15 (15mer, $T_M$=35° C.) and 732R16 (16mer, $T_m$=35° C.), were used, Sso7d-ΔTaq was more efficient than Taq, especially when the annealing temperature was high. The most striking difference between the two enzymes was observed with short primers, 57F12 (12mer) and 732R16 (16mer), where Sso7d-ΔTaq generated 10 times more products than Taq at both low and high annealing temperatures.

PCR using primers 57F12 (12 nt) and 732R16 (16 nt) were used to compare the efficiency of Sac7d-ΔTaq to the unmodified full length Taq in PCR reaction. Similar to Sso7d-ΔTaq, Sac7d-ΔTaq is significantly more efficient than Taq in amplifying using short primers.

A primer length assay was used to determine the ability of PL-ΔTaq to use short primers in PCR amplification. When long primers (57F and 732R) were used, the amplified product generated by PL-ΔTaq is ~50% of that by Sso7d-ΔTaq. When short primers (57F12 and 732R16) were used, the amplified product generated by PL-ΔTaq is <20% of that by Sso7d-ΔTaq.

TABLE 3

Comparison of the effect of primer length on PCR amplification by Sso7d-ΔTaq and Taq DNA polymerase.

| polymerase | 22 nt primer Anneal @55° C. | 22 nt primer Anneal @63° C. | 15 nt primer Anneal @49° C. | 15 nt primer Anneal @54° C. | 12 nt primer Anneal @49° C. | 12 nt primer Anneal @54° C. |
|---|---|---|---|---|---|---|
| Taq | 14000 | 9000 | 5500 | <500 | 1000 | undetectable |
| Sso7d-ΔTaq | 17000 | 13000 | 15000 | 5000 | 10000 | 3000 |
| Sso7d-ΔTaq:Taq | 1.2:1 | 1.4:1 | 2.7:1 | >10:1 | 10:1 | >10:1 |

Increased Performance of Fusion Polymerases in PCR Reactions

The increased stability and/or processivity of the fusion proteins of the invention provide increased efficiency in performing various modification reactions. For example, polymerase fusion proteins can provide more efficient amplification in PCR reactions. Many factors influence the outcome of a PCR reaction, including primer specificity, efficiency of the polymerase, quality, quantity and GC-content of the template, length of the amplicon, etc. Examples 5-8 demonstrate that fusion proteins that include a double-stranded sequence-non-specific nucleic acid binding domain, e.g., Sso7d, joined to a thermostable polymerase or polymerase domain have several advantageous features over the unmodified enzyme in PCR applications.

Example 5

Sso7d Fusion Proteins Exhibit a Higher and Broader Salt-Tolerance in PCR

The binding of polymerase to a primed DNA template is sensitive to the ionic strength of the reaction buffer due to electrostatic interactions, which is stronger in low salt concentration and weaker in high. The presence of Sso7d in a fusion polymerase protein stabilizes the binding interaction of the polymerase to DNA template. This example demonstrates that Sso7d fusion proteins exhibit improved performance in PCR reactions containing elevated KCl concentrations.

Lambda DNA (2 pM) was used as a template in a PCR reactions with primers 57F and 732R. The concentration of KCl was varied from 10 mM to 150 mM, while all other components of the reaction buffer were unchanged. The PCR reaction was carried out using a cycling program of 94° C. for 3 min, 20 cycles of 94° C. for 30 sec, 55° C. for 30 sec, and 72° C. for 30 sec, followed by 72° C. for 10 min. Upon completion of the reaction, 5 μl of the PCR reaction was removed and mixed with 195 μl of 1:400 dilution of PicoGreen in TE to quantify the amounts of amplicon generated. The PCR reaction products were also analyzed in parallel on an agarose gel to verify that amplicons of expected length were generated (data not shown). The effects of KCl concentration on the PCR efficiency of Sso7d-ΔTaq versus that of ΔTaq, and Pfu-Sso7d versus Pfu are shown in Table 4. The unmodified enzymes, ΔTaq and Pfu, showed a preference for KCl concentration below 25 mM and 40 mM, respectively, to maintain 80% of the maximum activity. In contrast, fusion proteins Sso7d-ΔTaq and Pfu-Sso7d maintain 80% of the maximum activity in 30-100 mM and 60-100 mM KCl, respectively. Thus, the Sso7d fusion proteins were more tolerant of elevated KCl concentration in comparison to their unmodified counter parts. This feature of the hybrid polymerase will potentially allow PCR amplification from low quality of DNA template, e.g., DNA samples prepared from, but not limited to, blood, food, and plant sources.

TABLE 4

Sso7d modification increases salt-tolerance of polymerase in PCR reaction

| Enzyme | Enzyme concentration | [KCl] for 80% activity |
|---|---|---|
| ΔTaq | 20 U/ml | <25 mM |
| Sso7d-ΔTaq | 20 U/ml | 30-100 mM |
| Pfu | 3 U/ml | <40 mM |
| Pfu-Sso7d | 12 U/ml* (equal molar) | 60-100 mM |

*Pfu-Sso7d has a 4-fold higher specific activity than Pfu. The specific activity is defined as unit/mol of enzyme.

Example 6

Sso7d-Fusion Polymerases are More Tolerant to SYBR Green I in Real-Time PCR

Three pairs of unmodified and modified enzymes were compared: commercial ΔTaq (ABI, Foster City, Calif.) vs. Sso7d-ΔTaq, Taq vs. Sso7d-Taq, and commercial Pfu (Stratagene, La Jolla Calif.) vs. Pfu-Sso7d. In addition to the 20 U/ml concentration used for all enzymes, a 5-fold higher concentration (100 U/ml) of ΔTaq and Pfu were used as well. The Ct values represent the number of cycles required to generate a detectable amount of DNA, and thus a lower Ct value reflects a greater amplification efficiency for the enzyme. Consistent Ct values are also preferable, indicating the reaction is robust to differences in dye concentration. Two extension times (10s and 30s) were used. The SYBR Green 1 concentration is indicated as 0.5×, etc. The 1×SYBR Green I is defined as a SYBR Green I solution in TE (10 mM Tris pH 7.5, 1 mM EDTA) that has an absorbance at 495 nm of 0.40±0.02. SYBR Green I was purchased from Molecular Probes (Eugene, Oreg.) as a 10,000× stock in DMSO. In all three pairs, the modified polymerase showed significantly higher tolerance of dye. The differences are most striking in the case of ΔTaq vs. Sso7d-ΔTaq.

TABLE 5

Sso7d fusion proteins are more tolerant of SYBR Green I.
(The symbol "—" indicates that no amplification was observed in 40 cycles

| | MgCl2 | 2 mM SYBR Green I | | | | | 3 mM SYBR Green I | | | | |
|---|---|---|---|---|---|---|---|---|---|---|---|
| ENZYMES | Unit/ml | 0.5x | 1x | 1.5x | 2x | 2.5x | 0.5x | 1x | 1.5x | 2x | 2.5x |
| | | 10 s @ 72° C. | | | | | | | | | |
| ΔTaq | 20 | — | — | — | — | — | — | — | — | — | — |
| ΔTaq | 100 | — | — | — | — | — | — | — | — | — | — |
| Sso7d-ΔTaq | 20 | 23.3 | 22.5 | 22.5 | 22.3 | 22.4 | 22.9 | 22.2 | 22 | 22.2 | 21.8 |
| Taq | 20 | 23 | 23.6 | — | — | — | 22.5 | 22.3 | 22.6 | — | — |
| Sso7d-Taq | 20 | 23.3 | 23.3 | 23.2 | 23.5 | — | 24 | 24 | 23.1 | 23.4 | 23.6 |
| Pfu | 20 | 31.2 | — | — | — | — | 31.5 | — | — | — | — |
| Pfu | 100 | 21.8 | 25 | — | — | — | 22.6 | 23.3 | 30 | — | — |
| Pfu-Sso7d | 20 | 21.5 | 22.3 | 35 | — | — | 21.8 | 22 | 22.6 | 27.2 | — |
| | | 30 s @ 72° C. | | | | | | | | | |
| ΔTaq | 20 | — | — | — | — | — | — | — | — | — | — |
| ΔTaq | 100 | — | — | — | — | — | 26.8 | — | — | — | — |
| Sso7d-ΔTaq | 20 | 23.8 | 22.3 | 22.6 | 21.8 | 21.7 | 22.3 | 21 | 21.3 | 21.8 | 21.8 |
| Taq | 20 | 24.2 | 24.6 | 29.4 | ∞ | — | 22.8 | 22.1 | 22.6 | 25 | — |
| Sso7d-Taq | 20 | 24.2 | 23.5 | 23 | 22.7 | 24.2 | 24.7 | 23.1 | 23.6 | 23.1 | 22.9 |
| Pfu | 20 | 33.2 | — | — | — | — | 29.4 | — | — | — | — |
| Pfu | 100 | 27.6 | 30.6 | — | — | — | 24.8 | 29.8 | — | — | — |
| Pfu-Sso7d | 20 | 25 | 24.8 | 25.4 | 24.4 | — | 23.1 | 25.3 | 23.6 | 26.1 | — |

Example 7

Sso7d-Fusion Polymerases are More Tolerant to Crude Template Preparations

A. Resistance to Bacterial Contamination in PCR

Colony PCR is a useful technique in which small samples of single bacterial colonies are lysed and added directly to PCR reactions for the purpose of screening the colonies for particular DNA sequences. Colony PCR has a high failure rate, presumably because of contaminants carries over from the colony. Polymerases resistant to cell extracts are desirable because they presumably will be more successful in colony PCR.

Materials for "Dirty" PCR

Lambda template (10 ng/ml): amplicon is a 891 bp fragment

Primers 56F/55R ($T_M$ 56° and 55°), 400 nM

Enzymes: Sst (Sso7d-ΔTaq) vs. PE Stf (ΔTaq), STq (Sso7d-Taq) vs. Taq-HIS or AmpliTaq or Amersham Taq, and Stratagene Pfu vs. PfS (Pfu-Sso7d) All enzymes are 20 U/ml except where indicated 200 μM each dNTP 2 mM $MgCl_2$, except 1.5 mM for Amersham Taq and AmpliTaq Reactions were 20 μl Methods:

*E. coli* were grown to saturation, spun down, suspended in water at an OD of 100, and frozen and thawed to disrupt cells. Dilutions of the disrupted bacteria were added at various concentrations to PCR reactions containing lambda DNA as template and two primers to amplify a 890 bp amplicon. 1× is equivalent to an OD of 10 (100D units/ml). The cycling conditions were as follows:

1) 95° C. –20"
2) 94° C. –5"
3) 60° C. –15"
4) 72° C. –45"
5) repeat steps 2–4 19 times
6) 72° C. –5'
7) 4° C. forever
8) END The experiment showed that Sso7d-ΔTaq significantly out performed Stoffel fragment (Applied Biosystems, Foster City, Calif.). Stoffel (Stf) is a trade name for a preparation of ΔTaq. Using 20 U/ml enzyme in the final reaction, Sso7d-ΔTaq allowed PCR amplification in the presence of 0.25× of cell dilution. When the same unit concentrations of Stoffel was used, no detectable product was generated, even in the most dilute cell solution. When 220 u/ml Stoffel was used, a detectable amount of product was generated at a 0.06× or lower concentration of the cell dilution. Thus, the resistance of Sso7d-ΔTaq to bacterial contamination in PCR reaction is more than 10-folder higher than that of the unmodified enzyme Stoffel.

Similarly, Pfu-Sso7d showed more resistance to bacterial contamination than Pfu, although both enzymes appeared to be more sensitive to the contamination than Taq-based enzymes. With 20 U/ml enzyme in the final reaction, Pfu allowed amplification only in the presence of 0.00006× or lower concentrations of cell dilution. In contrast, Pfu-Sso7d allowed efficient PCR amplification in 0.002× of cell dilution. Thus, Pfu-Sso7d has a 30-fold higher tolerance to bacterial contamination in PCR than the unmodified enzyme Pfu.

B. Resistance to Plant and Blood Contamination in PCR

Figure 1B:
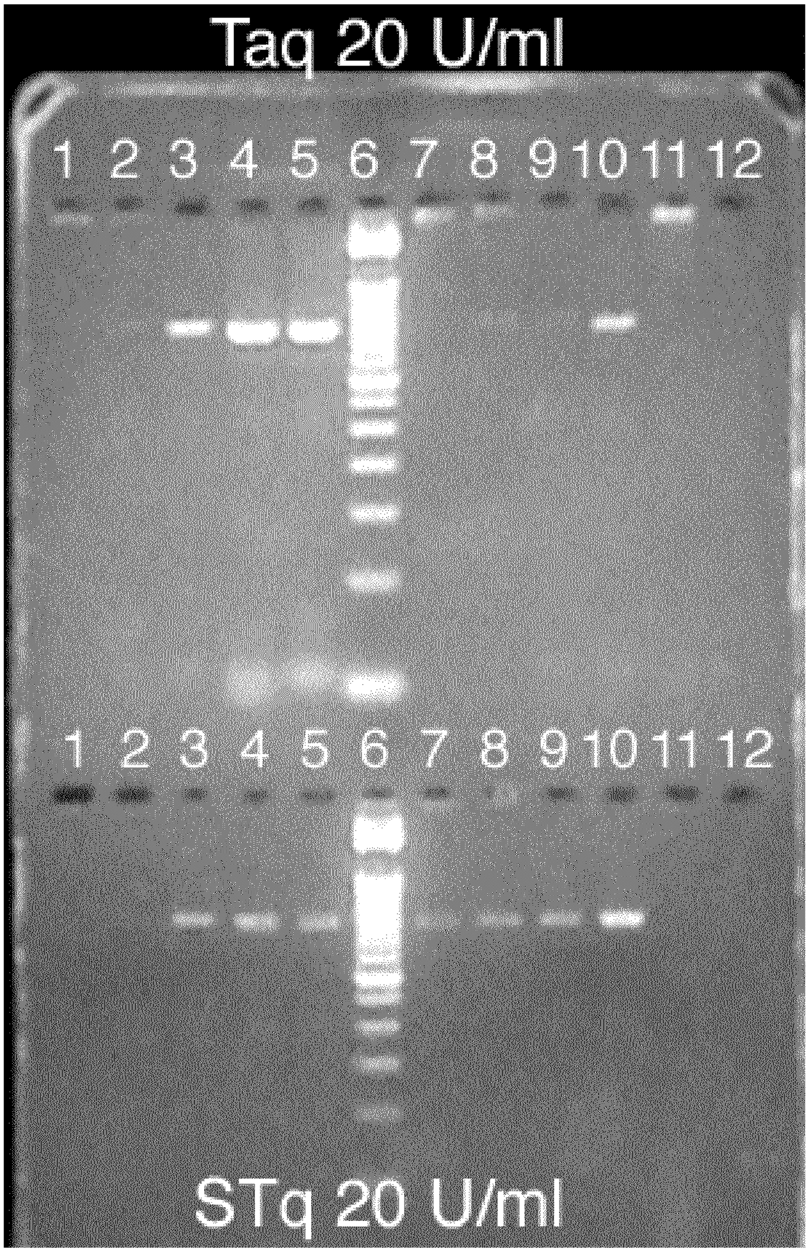

The same problems exist with other crude template preparations. PCR fails due to contaminants carried over in the template preparation. This example shows results with crude plant and blood preps. Dilution series were made of plant leaf homogenate from *Fritallaria agrestis*, a species of lily, and whole human blood. Dilutions were made with 1× TE, pH 8.0 at 1/10, 1/100, 1/1000. One microliter of a dilution was added to the appropriate reaction mix. The PCR cycling protocol was as follows:

94° C. 2 min
94° C. 10 sec
59° C. 20 sec for Taq & Sso7d-Taq (54° C. for Pfu & Pfu-Sso7d)
72° C. 30 sec
repeat cycle 34 times
72° C. 10 min The reaction products were analyzed on agarose gels (FIG. 1A and FIG. 1B). FIG. 1A shows a comparison of the contamination resistance of Pfu vs. PfS. Lanes 1-4 and 14-17 show progressive 10-fold dilutions of plant leaf homogenate. Pfu shows significant inhibition by a 1:10 dilution (lane 2), while PfS is completely resistant to this dilution (lane 7). Similarly, lanes 6-9 and 19-22 show progressive 10-fold dilutions of blood. Pfu is significantly inhibited by 1 microliter of blood, while PfS is resistant. Lanes 10 and 23 are positive controls (no plant or blood), while lanes 11 and 24 are negative controls (no plant or blood or template).

FIG. 1B shows a comparison between Taq and Sso7d-Taq. The upper panel shows reactions performed with 20 U/ml Taq, and the lower panel shows reactions performed with 20 U/ml Sso7d-Taq. Lanes 1-4 in each panel show progressive 10-fold dilutions of plant leaf homogenate and lanes 7-10 show progressive 10-fold dilutions of blood. Sso7d-Taq can amplify a product even in the presence of 1 μl whole blood, while Taq is inhibited by 100-fold less blood. Lanes 5 are positive controls (no plant or blood), while lanes 11 are negative controls (no plant or blood or template).

Example 8

Sso7d-Fusion Polymerases have Advantages in Cycle Sequencing

Plasmid clones encoding improved polymerases suitable for DNA sequencing have been constructed, and the protein products have been purified. and purified. The first enzyme is Sso7d-ΔTaq(Y), (SEQ ID No: 30 and 31 with mutations indicated in bold font) which is the same as the enzyme Sso7d-ΔTaq, except modified according to the method of Tabor and Richardson (U.S. Pat. No. 5,614,365) to have a "Y" substituted for an "F" residue at the indicated position in SEQ ID NO:31. The second enzyme is Sso7d-ΔTaq(E5;Y) (SEQ ID No: 32 and 33) with mutations indicated in bold font) which is the same as Sso7d-Taq, except modified according to the method of Tabor and Richardson and also containing point mutations that inactivate the 5'-3' nuclease domain.

The processivity of each Sso7d fusion polymerase was compared to its unmodified counterpart, i.e., the polymerase without the Sso7d domain. The results in Table 6 show that the Sso7d fusion polymerases are more processive.

TABLE 6

| Median Processivity Product Length at 10 mM KCl | |
|---|---|
| ΔTaq (Y) | 3 to 4 nts. |
| Sso7d-ΔTaq (Y) | 11 to 13 nts. |
| ΔTaq (E5)(Y) | 5 to 6 nts. |
| Sso7d-ΔTaq (E5)(Y) | 34 to 47 nts. |

Sequencing reactions using the fusion polymerases and their unmodified counterparts were performed by separating the components of a commercial sequencing kit (BigDye terminator Kit v.3, ABI, Foster City Calif.). Low-molecular-weight components were separated from the enzymes by ultrafiltration. Sequencing reactions performed by combining the low-molecular-weight fraction with the improved enzymes showed good signal strength vs. base number curves. Furthermore, the improved polymerases, e.g., Sso7d-ΔTaq(E5;Y), was able to continued through a hard stop better the other enzymes. Such an improved polymerase is also able to continue through dinucleotide, trinucletide, and long single base repeats more effectively than a counterpart polymerase.

Optimization of the sequencing reactions will demonstrate improvements in peak height evenness, contamination resistance, and lowered requirement for template and/or enzyme concentration.

Table of sequences

SEQ ID NO: 1 Synthetic Sso7d gene
GCAACCGTAAAGTTCAAGTACAAAGGCGAAGAAAAAGAGGTAGACATCTCCAAGATCAAGAAAGTAT -continued Table of sequences GGCGTGTGGGCAAGATGATCTCCTTCACCTACGACGAGGGCGGTGGCAAGACCGGCCGTGGTGCGGT
AAGCGAAAAGGACGCGCCGAAGGAGCTGCTGCAGATGCTGGAGAAGCAGAAAAAG SEQ ID NO: 2 The amino acid sequence of Sso7d
ATVKFKYKGEEKEVDISKIKKVWRVGKMISFTYDEGGGKTGRGAVSEKDAPKELLQMLEKQKK SEQ ID NO: 3 The DNA sequence encoding the Sso7d-ΔTaq fusion protein
ATGATTACGAATTCGAGCGCAACCGTAAAGTTCAAGTACAAAGGCGAAGAAAAAGAGGTAGACATCT
CCAAGATCAAGAAAGTATGGCGTGTGGGCAAGATGATCTCCTTCACCTACGACGAGGGCGGTGGCAA
GACCGGCCGTGGTGCGGTAAGCGAAAAGGACGCGCCGAAGGAGCTGCTGCAGATGCTGGAGAAGCAG
AAAAAGGGCGGCGGTGTCACTAGTCCCAAGGCcCTGGAGGAGGCCCCCTGGCCCCCGCCGGAAGGGG
CCTTCGTGGGCTTTGTGCTTTCCCGCAAGGAGCCCATGTGGGCCGATCTTCTGGCCCTGGCCGCCGC
CAGGGGGGGCCGGGTCCACCGGGCCCCCGAGCCTTATAAAGCCCTCAGGGACCTGAAGGAGGCGCGG
GGGCTTCTCGCCAAAGACCTGAGCGTTCTGGCCCTGAGGGAAGGCCTTGGCCTCCCGCCCGGCGACG
ACCCCATGCTCCTCGCCTACCTCCTGGACCCTTCCAACACCACCCCCGAGGGGGTGGCCCGGCGCTA
CGGCGGGGAGTGGACGGAGGAGGCGGGGGAGCGGGCCGCCCTTTCCGAGAGGCTCTTCGCCAACCTG
TGGGGGAGGCTTGAGGGGGAGGAGAGGCTCCTTTGGCTTTACCGGGAGGTGGAGAGGCCCCTTTCCG
CTGTCCTGGCCCACATGGAGGCCACGGGGGTGCGCCTGGACGTGGCCTATCTCAGGGCCTTGTCCCT
GGAGGTGGCCGAGGAGATCGCCCGCCTCGAGGCCGAGGTCTTCCGCCTGGCCGGCCACCCCTTCAAC
CTCAACTCCCGGGACCAGCTGGAAAGGGTCCTCTTTGACGAGCTAGGGCTTCCCGCCATCGGCAAGA
CGGAGAAGACCGGCAAGCGCTCCACCAGCGCCGCCGTCCTGGAGGCCCTCCGCGAGGCCCACCCCAT
CGTGGAGAAGATCCTGCAGTACCGGGAGCTCACCAAGCTGAAGAGCACCTACATTGACCCCTTGCCG
GACCTCATCCACCCCAGGACGGGCCGCCTCCACACCCGCTTCAACCAGACGGCCACGGCCACGGGCA
GGCTAAGTAGCTCCGATCCCAACCTCCAGAACATCCCCGTCCGCACCCCGCTTGGGCAGAGGATCCG
CCGGGCCTTCATCGCCGAGGAGGGGTGGCTATTGGTGGCCCTGGACTATAGCCAGATAGAGCTCAGG
GTGCTGGCCCACCTCTCCGGCGACGAGAACCTGATCCGGGTCTTCCAGGAGGGGCGGGACATCCACA
CGGAGACCGCCAGCTGGATGTTCGGCGTCCCCCGGGAGGCCGTGGACCCCCTGATGCGCCGGGCGGC
CAAGACCATCAACTTCGGGGTCCTCTACGGCATGTCGGCCCACCGCCTCTCCCAGGAGCTAGCCATC
CCTTACGAGGAGGCCCAGGCCTTCATTGAGCGCTACTTTCAGAGCTTCCCCAAGGTGCGGGCCTGGA
TTGAGAAGACCCTGGAGGAGGGCAGGAGGCGGGGGTACGTGGAGACCCTCTTCGGCCGCCGCCGCTA
CGTGCCAGACCTAGAGGCCCGGGTGAAGAGCGTGCGGGAGGCGGCCGAGCGCATGGCCTTCAACATG
CCCGTCCAGGGCACCGCCGCCGACCTCATGAAGCTGGCTATGGTGAAGCTCTTCCCCAGGCTGGAGG
AAATGGGGGCCAGGATGCTCCTTCAGGTCCACGACGAGCTGGTCCTCGAGGCCCCAAAAGAGAGGGC
GGAGGCCGTGGCCCGGCTGGCCAAGGAGGTCATGGAGGGGGTGTATCCCCTGGCCGTGCCCCTGGAG
GTGGAGGTGGGGATAGGGGAGGACTGGCTCTCCGCCAAGGAGGGCATTGATGGCCGCGGCGGAGGCG
GGCATCATCATCATCATCATTAA SEQ ID NO: 4 The amino acid sequence of Sso7d-ΔTaq fusion protein
MITNSSATVKFKYKGEEKEVDISKIKKVWRVGKMISFTYDEGGGKTGRGAVSEKDAPKELLQMLEKQ
KKGGGVTSPKALEEAPWPPPEGAFVGFVLSRKEPMWADLLALAAARGGRVHRAPEPYKALRDLKEAR
GLLAKDLSVLALREGLGLPPGDDPMLLAYLLDPSNTTPEGVARRYGGEWTEEAGERAALSERLFANL
WGRLEGEERLLWLYREVERPLSAVLAHMEATGVRLDVAYLRALSLEVAEEIARLEAEVFRLAGHPFN
LNSRDQLERVLFDELGLPAIGKTEKTGKRSTSAAVLEALREAHPIVEKILQYRELTKLKSTYIDPLP
DLIHPRTGRLHTRFNQTATATGRLSSSDPNLQNIPVRTPLGQRIRRAFIAEEGWLLVALDYSQIELR
VLAHLSGDENLIRVFQEGRDIHTETASWMFGVPREAVDPLMRRAAKTINFGVLYGMSAHRLSQELAI
PYEEAQAFIERYFQSFPKVRAWIEKTLEEGRRRGYVETLFGRRRYVPDLEARVKSVREAAERMAFNM
PVQGTAADLMKLAMVKLFPRLEEMGARMLLQVHDELVLEAPKERAEAVARLAKEVMEGVYPLAVPLE
VEVGIGEDWLSAKEGIDGRGGGGHHHHHH SEQ ID NO: 5 The DNA sequence encoding the Sso7d-Taq fusion protein
ATGATTACGAATTCGAGCGCAACCGTAAAGTTCAAGTACAAAGGCGAAGAAAAAGAGGTAGACATCT
CCAAGATCAAGAAAGTATGGCGTGTGGGCAAGATGATCTCCTTCACCTACGACGAGGGCGGTGGCAA
GACCGGCCGTGGTGCGGTAAGCGAAAAGGACGCGCCGAAGGAGCTGCTGCAGATGCTGGAGAAGCAG
AAAAAGGGCGGCGGTGTCACTAGTGGGATGCTGCCCCTCTTTGAGCCCAAGGGCCGGGTCCTCCTGG
TGGACGGCCACCACCTGGCCTACCGCACCTTCCACGCCCTGAAGGGCCTCACCACCAGCCGGGGGGA
GCCGGTGCAGGCGGTCTACGGCTTCGCCAAGAGCCTCCTCAAGGCCCTCAAGGAGGACGGGGACGCG
GTGATCGTGGTCTTTGACGCCAAGGCCCCCTCCTTCCGCCACGAGGCCTACGGGGGGTACAAGGCGG
GCCGGGCCCCCACGCCAGAGGACTTTCCCCGGCAACTCGCCCTCATCAAGGAGCTGGTGGACCTCCT
GGGGCTGGCGCGCCTCGAGGTCCCGGGCTACGAGGCGGACGACGTCCTGGCCAGCCTGGCCAAGAAG
GCGGAAAAGGAGGGCTACGAGGTCCGCATCCTCACCGCCGACAAAGACCTTTACCAGCTCCTTTCCG
ACCGCATCCACGTCCTCCACCCCGAGGGGTACCTCATCACCCCGGCCTGGCTTTGGGAAAAGTACGG
CCTGAGGCCCGACCAGTGGGCCGACTACCGGGCCCTGACCGGGGACGAGTCCGACAACCTTCCCGGG
GTCAAGGGCATCGGGGAGAAGACGGCGAGGAAGCTTCTGGAGGAGTGGGGGAGCCTGGAAGCCCTCC
TCAAGAACCTGGACCGGCTGAAGCCCGCCATCCGGGAGAAGATCCTGGCCCACATGGACGATCTGAA
GCTCTCCTGGGACCTGGCCAAGGTGCGCACCGACCTGCCCCTGGAGGTGGACTTCGCCAAAAGGCGG
GAGCCCGACCGGGAGAGGCTTAGGGCCTTTCTGGAGAGGCTTGAGTTTGGCAGCCTCCTCCACGAGT
TCGGCCTTCTGGAAAGCCCCAAGGCcCTGGAGGAGGCCCCCTGGCCCCCGCCGGAAGGGGCCTTCGT
GGGCTTTGTGCTTTCCCGCAAGGAGCCCATGTGGGCCGATCTTCTGGCCCTGGCCGCCGCCAGGGGG
GGCCGGGTCCACCGGGCCCCCGAGCCTTATAAAGCCCTCAGGGACCTGAAGGAGGCGCGGGGGCTTC
TCGCCAAAGACCTGAGCGTTCTGGCCCTGAGGGAAGGCCTTGGCCTCCCGCCCGGCGACGACCCCAT
GCTCCTCGCCTACCTCCTGGACCCTTCCAACACCACCCCCGAGGGGGTGGCCCGGCGCTACGGCGGG
GAGTGGACGGAGGAGGCGGGGGAGCGGGCCGCCCTTTCCGAGAGGCTCTTCGCCAACCTGTGGGGGA
GGCTTGAGGGGGAGGAGAGGCTCCTTTGGCTTTACCGGGAGGTGGAGAGGCCCCTTTCCGCTGTCCT
GGCCCACATGGAGGCCACGGGGGTGCGCCTGGACGTGGCCTATCTCAGGGCCTTGTCCCTGGAGGTG
GCCGAGGAGATCGCCCGCCTCGAGGCCGAGGTCTTCCGCCTGGCCGGCCACCCCTTCAACCTCAACT
CCCGGGACCAGCTGGAAAGGGTCCTCTTTGACGAGCTAGGGCTTCCCGCCATCGGCAAGACGGAGAA
GACCGGCAAGCGCTCCACCAGCGCCGCCGTCCTGGAGGCCCTCCGCGAGGCCCACCCCATCGTGGAG -continued Table of sequences AAGATCCTGCAGTACCGGGAGCTCACCAAGCTGAAGAGCACCTACATTGACCCCTTGCCGGACCTCA
TCCACCCCAGGACGGGCCGCCTCCACACCCGCTTCAACCAGACGGCCACGGCCACGGGCAGGCTAAG
TAGCTCCGATCCCAACCTCCAGAACATCCCCGTCCGCACCCCGCTTGGGCAGAGGATCCGCCGGGCC
TTCATCGCCGAGGAGGGGTGGCTATTGGTGGCCCTGGACTATAGCCAGATAGAGCTCAGGGTGCTGG
CCCACCTCTCCGGCGACGAGAACCTGATCCGGGTCTTCCAGGAGGGGCGGGACATCCACACGGAGAC
CGCCAGCTGGATGTTCGGCGTCCCCCGGGAGGCCGTGGACCCCCTGATGCGCCGGGCGGCCAAGACC
ATCAACTTCGGGGTCCTCTACGGCATGTCGGCCCACCGCCTCTCCCAGGAGCTAGCCATCCCTTACG
AGGAGGCCCAGGCCTTCATTGAGCGCTACTTTCAGAGCTTCCCCAAGGTGCGGGCCTGGATTGAGAA
GACCCTGGAGGAGGGCAGGAGGCGGGGGTACGTGGAGACCCTCTTCGGCCGCCGCCGCTACGTGCCA
GACCTAGAGGCCCGGGTGAAGAGCGTGCGGGAGGCGGCCGAGCGCATGGCCTTCAACATGCCCGTCC
AGGGCACCGCCGCCGACCTCATGAAGCTGGCTATGGTGAAGCTCTTCCCCAGGCTGGAGGAAATGGG
GGCCAGGATGCTCCTTCAGGTCCACGACGAGCTGGTCCTCGAGGCCCCAAAAGAGAGGGCGGAGGCC
GTGGCCCGGCTGGCCAAGGAGGTCATGGAGGGGGTGTATCCCCTGGCCGTGCCCCTGGAGGTGGAGG
TGGGGATAGGGGAGGACTGGCTCTCCGCCAAGGAGGGCATTGATGGCCGCGGCGGAGGCGGGCATCA
TCATCATCATCATTAA SEQ ID NO: 6 The amino acid sequence of Sso7d-Taq fusion protein
MITNSSATVKFKYKGEEKEVDISKIKKVWRVGKMISFTYDEGGGKTGRGAVSEKDAPKELLQMLEKQ
KKGGGVTSGMLPLFEPKGRVLLVDGHHLAYRTFHALKGLTTSRGEPVQAVYGFAKSLLKALKEDGDA
VIVVFDAKAPSFRHEAYGGYKAGRAPTPEDFPRQLALIKELVDLLGLARLEVPGYEADDVLASLAKK
AEKEGYEVRILTADKDLYQLLSDRIHVLHPEGYLITPAWLWEKYGLRPDQWADYRALTGDESDNLPG
VKGIGEKTARKLLEEWGSLEALLKNLDRLKPAIREKILAHMDDLKLSWDLAKVRTDLPLEVDFAKRR
EPDRERLRAFLERLEFGSLLHEFGLLESPKALEEAPWPPPEGAFVGFVLSRKEPMWADLLALAAARG
GRVHRAPEPYKALRDLKEARGLLAKDLSVLALREGLGLPPGDDPMLLAYLLDPSNTTPEGVARRYGG
EWTEEAGERAALSERLFANLWGRLEGEERLLWLYREVERPLSAVLAHMEATGVRLDVAYLRALSLEV
AEEIARLEAEVFRLAGHPFNLNSRDQLERVLFDELGLPAIGKTEKTGKRSTSAAVLEALREAHPIVE
KILQYRELTKLKSTYIDPLPDLIHPRTGRLHTRFNQTATATGRLSSSDPNLQNIPVRTPLGQRIRRA
FIAEEGWLLVALDYSQIELRVLAHLSGDENLIRVFQEGRDIHTETASWMFGVPREAVDPLMRRAAKT
INFGVLYGMSAHRLSQELAIPYEEAQAFIERYFQSFPKVRAWIEKTLEEGRRRGYVETLFGRRRYVP
DLEARVKSVREAAERMAFNMPVQGTAADLMKLAMVKLFPRLEEMGARMLLQVHDELVLEAPKERAEA
VARLAKEVMEGVYPLAVPLEVEVGIGEDWLSAKEGIDGRGGGGHHHHHH SEQ ID NO: 7 The DNA sequence encoding the Pfu-Sso7d fusion protein
ATGATTTTAGATGTGGATTACATAACTGAAGAAGGAAAACCTGTTATTAGGCTATTCAAAAAAGAGA
ACGGAAAATTTAAGATAGAGCATGATAGAACTTTTAGACCATACATTTACGCTCTTCTCAGGGATGA
TTCAAAGATTGAAGAAGTTAAGAAAATAACGGGGGAAAGGCATGGAAAGATTGTGAGAATTGTTGAT
GTAGAGAAGGTTGAGAAAAAGTTTCTCGGCAAGCCTATTACCGTGTGGAAACTTTATTTGGAACATC
CCCAAGATGTTCCCACTATTAGAGAAAAAGTTAGAGAACATCCAGCAGTTGTGGACATCTTCGAATA
CGATATTCCATTTGCAAAGAGATACCTCATCGACAAAGGCCTAATACCAATGGAGGGGGAAGAAGAG
CTAAAGATTCTTGCCTTCGATATAGAAACCCTCTATCACGAAGGAGAAGAGTTTGGAAAAGGCCCAA
TTATAATGATTAGTTATGCAGATGAAAATGAAGCAAAGGTGATTACTTGGAAAAACATAGATCTTCC
ATACGTTGAGGTTGTATCAAGCGAGAGAGAGATGATAAAGAGATTTCTCAGGATTATCAGGGAGAAG
GATCCTGACATTATAGTTACTTATAATGGAGACTCATTCGACTTCCCATATTTAGCGAAAAGGGCAG
AAAAACTTGGGATTAAATTAACCATTGGAAGAGATGGAAGCGAGCCCAAGATGCAGAGAATAGGCGA
TATGACGGCTGTAGAAGTCAAGGGAAGAATACATTTCGACTTGTATCATGTAATAACAAGGACAATA
AATCTCCCAACATACACACTAGAGGCTGTATATGAAGCAATTTTTGGAAAGCCAAAGGAGAAGGTAT
ACGCCGACGAGATAGCAAAAGCCTGGGAAAGTGGAGAGAACCTTGAGAGAGTTGCCAAATACTCGAT
GGAAGATGCAAAGGCAACTTATGAACTCGGGAAAGAATTCCTTCCAATGGAAATTCAGCTTTCAAGA
TTAGTTGGACAACCTTTATGGGATGTTTCAAGGTCAAGCACAGGGAACCTTGTAGAGTGGTTCTTAC
TTAGGAAAGCCTACGAAAGAAACGAAGTAGCTCCAAACAAGCCAAGTGAAGAGGAGTATCAAAGAAG
GCTCAGGGAGAGCTACACAGGTGGATTCGTTAAAGAGCCAGAAAAGGGGTTGTGGGAAAACATAGTA
TACCTAGATTTTAGAGCCCTATATCCCTCGATTATAATTACCCACAATGTTTCTCCCGATACTCTAA
ATCTTGAGGGATGCAAGAACTATGATATCGCTCCTCAAGTAGGCCACAAGTTCTGCAAGGACATCCC
TGGTTTTATACCAAGTCTCTTGGGACATTTGTTAGAGGAAAGACAAAAGATTAAGACAAAAATGAAG
GAAACTCAAGATCCTATAGAAAAAATACTCCTTGACTATAGACAAAAAGCGATAAAACTCTTAGCAA
ATTCTTTCTACGGATATTATGGCTATGCAAAAGCAAGATGGTACTGTAAGGAGTGTGCTGAGAGCGT
TACTGCCTGGGGAAGAAAGTACATCGAGTTAGTATGGAAGGAGCTCGAAGAAAAGTTTGGATTTAAA
GTCCTCTACATTGACACTGATGGTCTCTATGCAACTATCCCAGGAGGAGAAAGTGAGGAAATAAAGA
AAAAGGCTCTAGAATTTGTAAAATACATAAATTCAAAGCTCCCTGGACTGCTAGAGCTTGAATATGA
AGGGTTTTATAAGAGGGGATTCTTCGTTACGAAGAAGAGGTATGCAGTAATAGATGAAGAAGGAAAA
GTCATTACTCGTGGTTTAGAGATAGTTAGGAGAGATTGGAGTGAAATTGCAAAAGAAACTCAAGCTA
GAGTTTTGGAGACAATACTAAAACACGGAGATGTTGAAGAAGCTGTGAGAATAGTAAAAGAAGTAAT
ACAAAAGCTTGCCAATTATGAAATTCCACCAGAGAAGCTCGCAATATATGAGCAGATAACAAGACCA
TTACATGAGTATAAGGCGATAGGTCCTCACGTAGCTGTTGCAAAGAAACTAGCTGCTAAAGGAGTTA
AAATAAAGCCAGGAATGGTAATTGGATACATAGTACTTAGAGGCGATGGTCCAATTAGCAATAGGGC
AATTCTAGCTGAGGAATACGATCCCAAAAAGCACAAGTATGACGCAGAATATTACATTGAGAACCAG
GTTCTTCCAGCGGTACTTAGGATATTGGAGGGATTTGGATACAGAAAGGAAGACCTCAGATACCAAA
AGACAAGACAAGTCGGCCTAACTTCCTGGCTTAACATTAAAAAATCCGGTACCGGCGGTGGCGGTGC
AACCGTAAAGTTCAAGTACAAAGGCGAAGAAAAAGAGGTAGACATCTCCAAGATCAAGAAAGTATGG
CGTGTGGGCAAGATGATCTCCTTCACCTACGACGAGGGCGGTGGCAAGACCGGCCGTGGTGCGGTAA
GCGAAAAGGACGCGCCGAAGGAGCTGCTGCAGATGCTGGAGAAGCAGAAAAAGTGA SEQ ID NO: 8 The amino acid sequence of the Pfu-Sso7d fusion protein
MILDVDYITEEGKPVIRLFKKENGKFKIEHDRTFRPYIYALLRDDSKIEEVKKITGERHGKIVRIVD
VEKVEKKFLGKPITVWKLYLEHPQDVPTIREKVREHPAVVDIFEYDIPFAKRYLIDKGLIPMEGEEE
LKILAFDIETLYHEGEEFGKGPIIMISYADENEAKVITWKNIDLPYVEVVSSEREMIKRFLRIIREK
DPDIIVTYNGDSFDFPYLAKRAEKLGIKLTIGRDGSEPKMQRIGDMTAVEVKGRIHFDLYHVITRTI -continued Table of sequences NLPTYTLEAVYEAIFGKPKEKVYADEIAKAWESGENLERVAKYSMEDAKATYELGKEFLPMEIQLSR
LVGQPLWDVSRSSTGNLVEWFLLRKAYERNEVAPNKPSEEEYQRRLRESYTGGFVKEPEKGLWENIV
YLDFRALYPSIIITHNVSPDTLNLEGCKNYDIAPQVGHKFCKDIPGFIPSLLGHLLEERQKIKTKMK
ETQDPIEKILLDYRQKAIKLLANSFYGYYGYAKARWYCKECAESVTAWGRKYIELVWKELEEKFGFK
VLYIDTDGLYATIPGGESEEIKKKALEFVKYINSKLPGLLELEYEGFYKRGFFVTKKRYAVIDEEGK
VITRGLEIVRRDWSEIAKETQARVLETILKHGDVEEAVRIVKEVIQKLANYEIPPEKLAIYEQITRP
LHEYKAIGPHVAVAKKLAAKGVKIKPGMVIGYIVLRGDGPISNRAILAEEYDPKKHKYDAEYYIENQ
VLPAVLRILEGFGYRKEDLRYQKTRQVGLTSWLNIKKSGTGGGATVKFKYKGEEKEVDISKIKKVW
RVGKMISFTYDEGGGKTGRGAVSEKDAPKELLQMLEKQKK SEQ ID NO: 9 The DNA sequence encoding the Sac7d-ΔTaq fusion protein
ATGATTACGAATTCGACGGTGAAGGTAAAGTTCAAGTATAAGGGTGAAGAGAAAGAAGTAGACACTT
CAAAGATAAAGAAGGTTTGGAGAGTAGGCAAAATGGTGTCCTTTACCTATGACGACAATGGTAAGAC
AGGTAGAGGAGCTGTAAGCGAGAAAGATGCTCCAAAAGAATTATTAGACATGTTAGCAAGAGCAGAA
AGAGAGAAGAAAGGCGGCGGTGTCACTAGTCCCAAGGCCCTGGAGGAGGCCCCCTGGCCCCCGCCGG
AAGGGGCCTTCGTGGGCTTTGTGCTTTCCCGCAAGGAGCCCATGTGGGCCGATCTTCTGGCCCTGGC
CGCCGCCAGGGGGGGCCGGGTCCACCGGGCCCCCGAGCCTTATAAAGCCCTCAGGGACCTGAAGGAG
GCGCGGGGGCTTCTCGCCAAAGACCTGAGCGTTCTGGCCCTGAGGGAAGGCCTTGGCCTCCCGCCCG
GCGACGACCCCATGCTCCTCGCCTACCTCCTGGACCCTTCCAACACCACCCCCGAGGGGGTGGCCCG
GCGCTACGGCGGGGAGTGGACGGAGGAGGCGGGGGAGCGGGCCGCCCTTTCCGAGAGGCTCTTCGCC
AACCTGTGGGGGAGGCTTGAGGGGGAGGAGAGGCTCCTTTGGCTTTACCGGGAGGTGGAGAGGCCCC
TTTCCGCTGTCCTGGCCCACATGGAGGCCACGGGGGTGCGCCTGGACGTGGCCTATCTCAGGGCCTT
GTCCCTGGAGGTGGCCGAGGAGATCGCCCGCCTCGAGGCCGGGTCTTCCGCCTGGCCGGCCACCCCT
TCAACCTCAACTCCCGGGACCAGCTGGAAAGGGTCCTCTTTGACGAGCTAGGGCTTCCCGCCATCGG
CAAGACGGAGAAGACCGGCAAGCGCTCCACCAGCGCCGCCGTCCTGGAGGCCCTCCGCGAGGCCCAC
CCCATCGTGGAGAAGATCCTGCAGTACCGGGAGCTCACCAAGCTGAAGAGCACCTACATTGACCCCT
TGCCGGACCTCATCCACCCCAGGACGGGCCGCCTCCACACCCGCTTCAACCAGACGGCCACGGCCAC
GGGCAGGCTAAGTAGCTCCGATCCCAACCTCCAGAACATCCCCGTCCGCACCCCGCTTGGGCAGAGG
ATCCGCCGGGCCTTCATCGCCGAGGAGGGGTGGCTATTGGTGGCCCTGGACTATAGCCAGATAGAGC
TCAGGGTGCTGGCCCACCTCTCCGGCGACGAGAACCTGATCCGGGTCTTCCAGGAGGGGCGGGACAT
CCACACGGAGACCGCCAGCTGGATGTTCGGCGTCCCCCGGGAGGCCGTGGACCCCCTGATGCGCCGG
GCGGCCAAGACCATCAACTTCGGGGTCCTCTACGGCATGTCGGCCCACCGCCTCTCCCAGGAGCTAG
CCATCCCTTACGAGGAGGCCCAGGCCTTCATTGAGCGCTACTTTCAGAGCTTCCCCAAGGTGCGGGC
CTGGATTGAGAAGACCCTGGAGGAGGGCAGGAGGCGGGGGTACGTGGAGACCCTCTTCGGCCGCCGC
CGCTACGTGCCAGACCTAGAGGCCCGGGTGAAGAGCGTGCGGGAGGCGGCCGAGCGCATGGCCTTCA
ACATGCCCGTCCAGGGCACCGCCGCCGACCTCATGAAGCTGGCTATGGTGAAGCTCTTCCCCAGGCT
GGAGGAAATGGGGGCCAGGATGCTCCTTCAGGTCCACGACGAGCTGGTCCTCGAGGCCCCAAAAGAG
AGGGCGGAGGCCGTGGCCCGGCTGGCCAAGGAGGTCATGGAGGGGGTGTATCCCCTGGCCGTGCCCC
TGGAGGTGGAGGTGGGGATAGGGGAGGACTGGCTCTCCGCCAAGGAGGGCATTGATGGCCGCGGCGG
AGGCGGGCATCATCATCATCATCATTAA SEQ ID NO: 10 The amino acid sequence of the Sac7d-ΔTaq fusion protein
MITNSTVKVKFKYKGEEKEVDTSKIKKVWRVGKMVSFTYDDNGKTGRGAVSEKDAPKELLDMLARAE
REKKGGGVTSPKALEEAPWPPPEGAFVGFVLSRKEPMWADLLALAAARGGRVHRAPEPYKALRDLKE
ARGLLAKDLSVLALREGLGLPPGDDPMLLAYLLDPSNTTPEGVARRYGGEWTEEAGERAALSERLFA
NLWGRLEGEERLLWLYREVERPLSAVLAHMEATGVRLDVAYLRALSLEVAEEIARLEAEVFRLAGHP
FNLNSRDQLERVLFDELGLPAIGKTEKTGKRSTSAAVLEALREAHPIVEKILQYRELTKLKSTYIDP
LPDLIHPRTGRLHTRFNQTATATGRLSSSDPNLQNIPVRTPLGQRIRRAFIAEEGWLLVALDYSQIE
LRVLAHLSGDENLIRVFQEGRDIHTETASWMFGVPREAVDPLMRRAAKTINFGVLYGMSAHRLSQEL
AIPYEEAQAFIERYFQSFPKVRAWIEKTLEEGRRRGYVETLFGRRRYVPDLEARVKSVREAAERMAF
NMPVQGTAADLMKLAMVKLFPRLEEMGARMLLQVHDELVLEAPKERAEAVARLAKEVMEGVYPLAVP
LEVEVGIGEDWLSAKEGIDGRGGGHHHHHH SEQ ID NO: 11 The DNA sequence encoding the PL-ΔTaq fusion protein
ATGATTACGAATTCGAAGAAAAAGAAAAAGAAAAAGCGTAAGAAACGCAAAAAGAAAAAGAAAGGCG
GCGGTGTCACTAGTGGCGCAACCGTAAAGTTCAAGTACAAAGGCGAAGAAAAAGAGGTAGACATCTC
CAAGATCAAGAAAGTATGGCGTGTGGGCAAGATGATCTCCTTCACCTACGACGAGGGCGGTGGCAAG
ACCGGCCGTGGTGCGGTAAGCGAAAAGGACGCGCCGAAGGAGCTGCTGCAGATGCTGGAGAAGCAGA
AAAAGGGCGGCGGTGTCACCAGTCCCAAGGCCCTGGAGGAGGCCCCCTGGCCCCCGCCGGAAGGGGC
CTTCGTGGGCTTTGTGCTTTCCCGCAAGGAGCCCATGTGGGCCGATCTTCTGGCCCTGGCCGCCGCC
AGGGGGGGCCGGGTCCACCGGGCCCCCGAGCCTTATAAAGCCCTCAGGGACCTGAAGGAGGCGCGGG
GGCTTCTCGCCAAAGACCTGAGCGTTCTGGCCCTGAGGGAAGGCCTTGGCCTCCCGCCCGGCGACGA
CCCCATGCTCCTCGCCTACCTCCTGGACCCTTCCAACACCACCCCCGAGGGGGTGGCCCGGCGCTAC
GGCGGGGAGTGGACGGAGGAGGCGGGGGAGCGGGCCGCCCTTTCCGAGAGGCTCTTCGCCAACCTGT
GGGGGAGGCTTGAGGGGGAGGAGAGGCTCCTTTGGCTTTACCGGGAGGTGGAGAGGCCCCTTTCCGC
TGTCCTGGCCCACATGGAGGCCACGGGGGTGCGCCTGGACGTGGCCTATCTCAGGGCCTTGTCCCTG
GAGGTGGCCGAGGAGATCGCCCGCCTCGAGGCCGAGGTCTTCCGCCTGGCCGGCCACCCCTTCAACC
TCAACTCCCGGGACCAGCTGGAAAGGGTCCTCTTTGACGAGCTAGGGCTTCCCGCCATCGGCAAGAC
GGAGAAGACCGGCAAGCGCTCCACCAGCGCCGCCGTCCTGGAGGCCCTCCGCGAGGCCCACCCCATC
GTGGAGAAGATCCTGCAGTACCGGGAGCTCACCAAGCTGAAGAGCACCTACATTGACCCCTTGCCGG
ACCTCATCCACCCCAGGACGGGCCGCCTCCACACCCGCTTCAACCAGACGGCCACGGCCACGGGCAG
GCTAAGTAGCTCCGATCCCAACCTCCAGAACATCCCCGTCCGCACCCCGCTTGGGCAGAGGATCCGC
CGGGCCTTCATCGCCGAGGAGGGGTGGCTATTGGTGGCCCTGGACTATAGCCAGATAGAGCTCAGGG
TGCTGGCCCACCTCTCCGGCGACGAGAACCTGATCCGGGTCTTCCAGGAGGGGCGGGACATCCACAC
GGAGACCGCCAGCTGGATGTTCGGCGTCCCCCGGGAGGCCGTGGACCCCCTGATGCGCCGGGCGGCC
AAGACCATCAACTTCGGGGTCCTCTACGGCATGTCGGCCCACCGCCTCTCCCAGGAGCTAGCCATCC -continued Table of sequences CTTACGAGGAGGCCCAGGCCTTCATTGAGCGCTACTTTCAGAGCTTCCCCAAGGTGCGGGCCTGGAT
TGAGAAGACCCTGGAGGAGGGCAGGAGGCGGGGGTACGTGGAGACCCTCTTCGGCCGCCGCCGCTAC
GTGCCAGACCTAGAGGCCCGGGTGAAGAGCGTGCGGGAGGCGGCCGAGCGCATGGCCTTCAACATGC
CCGTCCAGGGCACCGCCGCCGACCTCATGAAGCTGGCTATGGTGAAGCTCTTCCCCAGGCTGGAGGA
AATGGGGGCCAGGATGCTCCTTCAGGTCCACGACGAGCTGGTCCTCGAGGCCCCAAAAGAGAGGGCG
GAGGCCGTGGCCCGGCTGGCCAAGGAGGTCATGGAGGGGGTGTATCCCCTGGCCGTGCCCCTGGAGG
TGGAGGTGGGGATAGGGGAGGACTGGCTCTCCGCCAAGGAGGGCATTGATGGCCGCGGCGGAGGCGG
GCATCATCATCATCATCATTAA SEQ ID NO: 12 The amino acid sequence of PL-ΔTaq fusion protein
MITNSKKKKKKKRKKRKKKKKGGGVTSGATVKFKYKGEEKEVDISKIKKVWRVGKMISFTYDEGGGK
TGRGAVSEKDAPKELLQMLEKQKKGGGVTSPKALEEAPWPPPEGAFVGFVLSRKEPMWADLLALAAA
RGGRVHRAPEPYKALRDLKEARGLLAKDLSVLALREGLGLPPGDDPMLLAYLLDPSNTTPEGVARRY
GGEWTEEAGERAALSERLFANLWGRLEGEERLLWLYREVERPLSAVLAHMEATGVRLDVAYLRALSL
EVAEEIARLEAEVFRLAGHPFNLNSRDQLERVLFDELGLPAIGKTEKTGKRSTSAAVLEALREAHPI
VEKILQYRELTKLKSTYIDPLPDLIHPRTGRLHTRFNQTATATGRLSSSDPNLQNIPVRTPLGQRIR
RAFIAEEGWLLVALDYSQIELRVLAHLSGDENLIRVFQEGRDIHTETASWMFGVPREAVDPLMRRAA
KTINFGVLYGMSAHRLSQELAIPYEEAQAFIERYFQSFPKVRAWIEKTLEEGRRRGYVETLFGRRRY
VPDLEARVKSVREAAERMAFNMPVQGTAADLMKLAMVKLFPRLEEMGARMLLQVHDELVLEAPKERA
EAVARLAKEVMEGVYPLAVPLEVEVGIGEDWLSAKEGIDGRGGGHHHHHH

SEQ ID NO: 13 PRIMER L71F
5'-CCTGCTCTGCCGCTTCACGC-3'

SEQ ID NO: 14 PRIMER L71R
5'-GCACAGCGGCTGGCTGAGGA-3'

SEQ ID NO: 15 PRIMER L18015F
5'-TGACGGAGGATAACGCCAGCAG-3'

SEQ ID NO: 16 PRIMER L23474R
5'-GAAAGACGA TGGGTCGCTAATACGC-3'

SEQ ID NO: 17 PRIMER L18015F
5'-TGACGGAGGATAAC GCCAGCAG-3'

SEQ ID NO: 18 PRIMER L29930R
5'-GGGGTTGGAGGTCAATGGGTTC-3'

SEQ ID NO: 19 PRIMER L30350F
5'-CCTGCTCTGCCGCTTCACGC-3'

SEQ ID NO: 20 PRIMER L35121R
5'-CACATGGTACAGCAAGCCTGGC-3'

SEQ ID NO: 21 PRIMER L2089F
5'-CCCGTATCTGCTGGGA TACTGGC-3

SEQ ID NO: 22 PRIMER L7112R
5'-CAGCGGTGCTGACTGAATCATGG-3

SEQ ID NO: 23 PRIMER L30350F
5'-CCTGCCTGCCGCTTCACGC-3'

SEQ ID NO: 24 PRIMER L40547R
5'-CCAATACCCGTTTCA TCGCGGC-3'

SEQ ID NO: 25 PRIMER H-Amelo-Y
5'-CCACCTCATCCTGG GCACC-3'

SEQ ID NO: 26 PRIMER H-Amelo-YR
5'-GCTTGAGGCCAACCATCAGAGC-3'

SEQ ID NO: 27 Human beta-globin primer 536F
5'-GGTTGGCCAATCTACTCCCAGG-3'

SEQ ID NO: 28 Human beta-globin primer 536R
5'-GCTCACTCAGTGTGGCAAAG-3'

SEQ ID NO: 29 Human beta-globin primer 1408R
5'-GATTAGCAAAAGGGCCTAGCTTGG-3'

SEQ ID NO: 30 The DNA sequence encoding the Sso7d-ΔTaq(Y) protein
ATGATTACGAATTCGAGCGCAACCGTAAAGTTCAAGTACAAAGGCGAAGAAAAAGAGGTAGACATCT
CCAAGATCAAGAAAGTATGGCGTGTGGGCAAGATGATCTCCTTCACCTACGACGAGGGCGGTGGCAA
GACCGGCCGTGGTGCGGTAAGCGAAAAGGACGCGCCGAAGGAGCTGCTGCAGATGCTGGAGAAGCAG
AAAAAGGGCGGCGGTGTCACTAGTCCCAAGGCcCTGGAGGAGGCCCCCTGGCCCCCGCCGGAAGGGG -continued Table of sequences CCTTCGTGGGCTTTGTGCTTTCCCGCAAGGAGCCCATGTGGGCCGATCTTCTGGCCCTGGCCGCCGC
CAGGGGGGGCCGGGTCCACCGGGCCCCCGAGCCTTATAAAGCCCTCAGGGACCTGAAGGAGGCGCGG
GGGCTTCTCGCCAAAGACCTGAGCGTTCTGGCCCTGAGGGAAGGCCTTGGCCTCCCGCCCGGCGACG
ACCCCATGCTCCTCGCCTACCTCCTGGACCCTTCCAACACCACCCCCGAGGGGGTGGCCCGGCGCTA
CGGCGGGGAGTGGACGGAGGAGGCGGGGGAGCGGGCCGCCCTTTCCGAGAGGCTCTTCGCCAACCTG
TGGGGGAGGCTTGAGGGGGAGGAGAGGCTCCTTTGGCTTTACCGGGAGGTGGAGAGGCCCCTTTCCG
CTGTCCTGGCCCACATGGAGGCCACGGGGGTGCGCCTGGACGTGGCCTATCTCAGGGCCTTGTCCCT
GGAGGTGGCCGAGGAGATCGCCCGCCTCGAGGCCGAGGTCTTCCGCCTGGCCGGCCACCCCTTCAAC
CTCAACTCCCGGGACCAGCTGGAAAGGGTCCTCTTTGACGAGCTAGGGCTTCCCGCCATCGGCAAGA
CGGAGAAGACCGGCAAGCGCTCCACCAGCGCCGCCGTCCTGGAGGCCCTCCGCGAGGCCCACCCCAT
CGTGGAGAAGATCCTGCAGTACCGGGAGCTCACCAAGCTGAAGAGCACCTACATTGACCCCTTGCCG
GACCTCATCCACCCCAGGACGGGCCGCCTCCACACCCGCTTCAACCAGACGGCCACGGCCACGGGCA
GGCTAAGTAGCTCCGATCCCAACCTCCAGAACATCCCCGTCCGCACCCCGCTTGGGCAGAGGATCCG
CCGGGCCTTCATCGCCGAGGAGGGGTGGCTATTGGTGGCCCTGGACTATAGCCAGATAGAGCTCAGG
GTGCTGGCCCACCTCTCCGGCGACGAGAACCTGATCCGGGTCTTCCAGGAGGGGCGGGACATCCACA
CGGAGACCGCCAGCTGGATGTTCGGCGTCCCCCGGGAGGCCGTGGACCCCCTGATGCGCCGGGCGGC
CAAGACCATCAACTACGGGGTCCTCTACGGCATGTCGGCCCACCGCCTCTCCCAGGAGCTAGCCATC
CCTTACGAGGAGGCCCAGGCCTTCATTGAGCGCTACTTTCAGAGCTTCCCCAAGGTGCGGGCCTGGA
TTGAGAAGACCCTGGAGGAGGGCAGGAGGCGGGGGTACGTGGAGACCCTCTTCGGCCGCCGCCGCTA
CGTGCCAGACCTAGAGGCCCGGGTGAAGAGCGTGCGGGAGGCGGCCGAGCGCATGGCCTTCAACATG
CCCGTCCAGGGCACCGCCGCCGACCTCATGAAGCTGGCTATGGTGAAGCTCTTCCCCAGGCTGGAGG
AAATGGGGGCCAGGATGCTCCTTCAGGTCCACGACGAGCTGGTCCTCGAGGCCCCAAAAGAGAGGGC
GGAGGCCGTGGCCCGGCTGGCCAAGGAGGTCATGGAGGGGGTGTATCCCCTGGCCGTGCCCCTGGAG
GTGGAGGTGGGGATAGGGGAGGACTGGCTCTCCGCCAAGGAGGGCATTGATGGCCGCGGCGGAGGCG
GGCATCATCATCATCATCATTAA SEQ ID NO: 31 The amino acid sequence of Sso7d-ΔTaq(Y) protein
MITNSSATVKFKYKGEEKEVDISKIKKVWRVGKMISFTYDEGGGKTGRGAVSEKDAPKELLQMLEKQ
KKGGGVTSPKALEEAPWPPPEGAFVGFVLSRKEPMWADLLALAAARGGRVHRAPEPYKALRDLKEAR
GLLAKDLSVLALREGLGLPPGDDPMLLAYLLDPSNTTPEGVARRYGGEWTEEAGERAALSERLFANL
WGRLEGEERLLWLYREVERPLSAVLAHMEATGVRLDVAYLRALSLEVAEEIARLEAEVFRLAGHPFN
LNSRDQLERVLFDELGLPAIGKTEKTGKRSTSAAVLEALREAHPIVEKILQYRELTKLKSTYIDPLP
DLIHPRTGRLHTRFNQTATATGRLSSSDPNLQNIPVRTPLGQRIRRAFIAEEGWLLVALDYSQIELR
VLAHLSGDENLIRVFQEGRDIHTETASWMFGVPREAVDPLMRRAAKTINYGVLYGMSAHRLSQELAI
PYEEAQAFIERYFQSFPKVRAWIEKTLEEGRRRGYVETLFGRRRYVPDLEARVKSVREAAERMAFNM
PVQGTAADLMKLAMVKLFPRLEEMGARMLLQVHDELVLEAPKERAEAVARLAKEVMEGVYPLAVPLE
VEVGIGEDWLSAKEGIDGRGGGGHHHHHH SEQ ID NO: 32 The DNA sequence encoding the Sso7d-ΔTaq (E5)(Y)
protein
ATGATTACGAATTCGAGCGCAACCGTAAAGTTCAAGTACAAAGGCGAAGAAAAAGAGGTAGACATCT
CCAAGATCAAGAAAGTATGGCGTGTGGGCAAGATGATCTCCTTCACCTACGACGAGGGCGGTGGCAA
GACCGGCCGTGGTGCGGTAAGCGAAAAGGACGCGCCGAAGGAGCTGCTGCAGATGCTGGAGAAGCAG
AAAAAGGGCGGCGGTGTCACTAGTGGGATGCTGCCCCTCTTTGAGCCCAAGGGCCGGGTCCTCCTGG
TGGACGGCCACCACCTGGCCTACCGCACCTTCCACGCCCTGAAGGGCCTCACCACCAGCCGGGGGGA
GCCGGTGCAGGCGGTCTACGGCTTCGCCAAGAGCCTCCTCAAGGCCCTCAAGGAGGACGGGGACGCG
GTGATCGTGGTCTTTGACGCCAAGGCCCCCTCCTTCCCCCACGAGGCCTACGGGGGGCACAAGGCGG
GCCGGGCCCCCACGCCAGAGGACTTTCCCCGGCAACTCGCCCTCATCAAGGAGCTGGTGGACCTCCT
GGGGCTGGCGCGCCTCGAGGTCCCGGGCTACGAGGCGGACGACGTCCTGGCCAGCCTGGCCAAGAAG
GCGGAAAAGGAGGGCTACGAGGTCCGCATCCTCACCGCCGACAAAGACCTTTACCAGCTCCTTTCCG
ACCGCATCCACGTCCTCCACCCCGAGGGGTACCTCATCACCCCGGCCTGGCTTTGGGAAAAGTACGG
CCTGAGGCCCGACCAGTGGGCCGACTACCGGGCCCTGACCGGGGACGAGTCCGACAACCTTCCCGGG
GTCAAGGGCATCGGGGAGAAGACGGCGAGGAAGCTTCTGGAGGAGTGGGGGAGCCTGGAAGCCCTCC
TCAAGAACCTGGACCGGCTGAAGCCCGCCATCCGGGAGAAGATCCTGGCCCACATGGACGATCTGAA
GCTCTCCTGGGACCTGGCCAAGGTGCGCACCGACCTGCCCCTGGAGGTGGACTTCGCCAAAAGGCGG
GAGCCCGACCGGGAGAGGCTTAGGGCCTTTCTGGAGAGGCTTGAGTTTGGCAGCCTCCTCCACGAGT
TCGGCCTTCTGGAAAGCCCCAAGGCcCTGGAGGAGGCCCCCTGGCCCCCGCCGGAAGGGGCCTTCGT
GGGCTTTGTGCTTTCCCGCAAGGAGCCCATGTGGGCCGATCTTCTGGCCCTGGCCGCCGCCAGGGGG
GGCCGGGTCCACCGGGCCCCCGAGCCTTATAAAGCCCTCAGGGACCTGAAGGAGGCGCGGGGGCTTC
TCGCCAAAGACCTGAGCGTTCTGGCCCTGAGGGAAGGCCTTGGCCTCCCGCCCGGCGACGACCCCAT
GCTCCTCGCCTACCTCCTGGACCCTTCCAACACCACCCCCGAGGGGGTGGCCCGGCGCTACGGCGGG
GAGTGGACGGAGGAGGCGGGGGAGCGGGCCGCCCTTTCCGAGAGGCTCTTCGCCAACCTGTGGGGGA
GGCTTGAGGGGGAGGAGAGGCTCCTTTGGCTTTACCGGGAGGTGGAGAGGCCCCTTTCCGCTGTCCT
GGCCCACATGGAGGCCACGGGGGTGCGCCTGGACGTGGCCTATCTCAGGGCCTTGTCCCTGGAGGTG
GCCGAGGAGATCGCCCGCCTCGAGGCCGAGGTCTTCCGCCTGGCCGGCCACCCCTTCAACCTCAACT
CCCGGGACCAGCTGGAAAGGGTCCTCTTTGACGAGCTAGGGCTTCCCGCCATCGGCAAGACGGAGAA
GACCGGCAAGCGCTCCACCAGCGCCGCCGTCCTGGAGGCCCTCCGCGAGGCCCACCCCATCGTGGAG
AAGATCCTGCAGTACCGGGAGCTCACCAAGCTGAAGAGCACCTACATTGACCCCTTGCCGGACCTCA
TCCACCCCAGGACGGGCCGCCTCCACACCCGCTTCAACCAGACGGCCACGGCCACGGGCAGGCTAAG
TAGCTCCGATCCCAACCTCCAGAACATCCCCGTCCGCACCCCGCTTGGGCAGAGGATCCGCCGGGCC
TTCATCGCCGAGGAGGGGTGGCTATTGGTGGCCCTGGACTATAGCCAGATAGAGCTCAGGGTGCTGG
CCCACCTCTCCGGCGACGAGAACCTGATCCGGGTCTTCCAGGAGGGGCGGGACATCCACACGGAGAC
CGCCAGCTGGATGTTCGGCGTCCCCCGGGAGGCCGTGGACCCCCTGATGCGCCGGGCGGCCAAGACC
ATCAACTACGGGGTCCTCTACGGCATGTCGGCCCACCGCCTCTCCCAGGAGCTAGCCATCCCTTACG
AGGAGGCCCAGGCCTTCATTGAGCGCTACTTTCAGAGCTTCCCCAAGGTGCGGGCCTGGATTGAGAA
GACCCTGGAGGAGGGCAGGAGGCGGGGGTACGTGGAGACCCTCTTCGGCCGCCGCCGCTACGTGCCA
GACCTAGAGGCCCGGGTGAAGAGCGTGCGAGGCGGCCGAGCGCATGGCCTTCAACATGCCGGCGTCC -continued

| Table of sequences |
|---|
| AGGGCACCGCCGCCGACCTCATGAAGCTGGCTATGGTGAAGCTCTTCCCCAGGCTGGAGGAAATGGG<br>GGCCAGGATGCTCCTTCAGGTCCACGACGAGCTGGTCCTCGAGGCCCCAAAAGAGAGGGCGGAGGCC<br>GTGGCCCGGCTGGCCAAGGAGGTCATGGAGGGGGTGTATCCCCTGGCCGTGCCCCTGGAGGTGGAGG<br>TGGGGATAGGGGAGGACTGGCTCTCCGCCAAGGAGGGCATTGATGGCCGCGGCGGAGGCGGGCATCA<br>TCATCATCATCATTAA |
| SEQ ID NO: 33 The amino acid sequence of Sso7d-ΔTaq (E5)(Y) protein<br>MITNSSATVKFKYKGEEKEVDISKIKKVWRVGKMISFTYDEGGGKTGRGAVSEKDAPKELLQMLEKQ<br>KKGGGVTSGMLPLFEPKGRVLLVDGHHLAYRTFHALKGLTTSRGEPVQAVYGFAKSLLKALKEDGDA<br>VIVVFDAKAPSF**P**HEAYGG**H**KAGRAPTPEDFPRQLALIKELVDLLGLARLEVPGYEADDVLASLAKK<br>AEKEGYEVRILTADKDLYQLLSDRIHVLHPEGYLITPAWLWEKYGLRPDQWADYRALTGDESDNLPG<br>VKGIGEKTARKLLEEWGSLEALLKNLDRLKPAIREKILAHMDDLKLSWDLAKVRTDLPLEVDFAKRR<br>EPDRERLRAFLERLEFGSLLHEFGLLESPKALEEAPWPPPEGAFVGFVLSRKEPMWADLLALAAARG<br>GRVHRAPEPYKALRDLKEARGLLAKDLSVLALREGLGLPPGDDPMLLAYLLDPSNTTPEGVARRYGG<br>EWTEEAGERAALSERLFANLWGRLEGEERLLWLYREVERPLSAVLAHMEATGVRLDVAYLRALSLEV<br>AEEIARLEAEVFRLAGHPFNLNSRDQLERVLFDELGLPAIGKTEKTGKRSTSAAVLEALREAHPIVE<br>KILQYRELTKLKSTYIDPLPDLIHPRTGRLHTRFNQTATATGRLSSSDPNLQNIPVRTPLGQRIRRA<br>FIAEEGWLLVALDYSQIELRVLAHLSGDENLIRVFQEGRDIHTETASWMFGVPREAVDPLMRRAAKT<br>IN**Y**GVLYGMSAHRLSQELAIPYEEAQAFIERYFQSFPKVRAWIEKTLEEGRRRGYVETLFGRRRYVP<br>DLEARVKSVREAAERMAFNMPVQGTAADLMKLAMVKLFPRLEEMGARMLLQVHDELVLEAPKERAEA<br>VARLAKEVMEGVYPLAVPLEVEVGIGEDWLSAKEGIDGRGGGGHHHHHH |

What is claimed is:

1. A method of sequencing a target nucleic acid in an aqueous solution using an improved DNA polymerase, the method comprising:

(a) contacting the target nucleic acid with a thermally stable DNA polymerase, wherein the DNA polymerase is joined to a sequence non-specific double-stranded nucleic acid binding domain that comprises at least 75% amino acid sequence identity to the Sso7d amino acid sequence set forth in SEQ ID NO:2, and enhances the processivity of the DNA polymerase compared to an identical DNA polymerase not having the sequence non-specific double-stranded nucleic acid binding domain fused to it, and wherein the solution is of a composition that permits the sequence non-specific double-stranded nucleic acid binding domain to bind to the target nucleic acid and the polymerase domain to extend a primer that is hybridized to the target nucleic acid sequence;

(b) incubating the solution under conditions in which the primer is extended by the DNA polymerase; and (c) identifying the nucleotides that are incorporated into the synthesized nucleic acid strand upon the template-dependent extension of the primer by the DNA polymerase, thereby sequencing the nucleic acid.

2. The method of claim 1, wherein the thermally stable DNA polymerase has a ΔTaq polymerase domain.

3. The method of claim 1, wherein the sequence non-specific double-stranded nucleic acid binding domain comprises at least 90% amino acid sequence identity to the Sso7d amino acid sequence set forth in SEQ ID NO:2.

4. The method of claim 1, wherein the sequence non-specific double-stranded nucleic acid binding domain comprises Sso7d (SEQ ID NO:2) or Sac7d (amino acids 7-71 of SEQ ID NO:10).

5. A method of sequencing a target nucleic acid in an aqueous solution using an improved DNA polymerase, the method comprising:

(a) contacting the target nucleic acid with a thermally stable DNA polymerase, wherein the DNA polymerase is joined to a sequence non-specific double-stranded nucleic acid binding domain that specifically binds to polyclonal antibodies generated against either Sso7d (SEQ ID NO:2) or Sac7d (amino acids 7-71 of SEQ ID NO:10), and enhances the processivity of the DNA polymerase compared to an identical DNA polymerase not having the sequence non-specific double-stranded nucleic acid binding domain fused to it, and wherein the solution is of a composition that permits the sequence non-specific double-stranded nucleic acid binding domain to bind to the target nucleic acid and the polymerase domain to extend a primer that is hybridized to the target nucleic acid sequence;

(b) incubating the solution under conditions in which the primer is extended by the DNA polymerase; and (c) identifying the nucleotides that are incorporated into the synthesized nucleic acid strand upon the template-dependent extension of the primer by the DNA polymerase, thereby sequencing the nucleic acid.

6. The method of claim 5, wherein the thermally stable DNA polymerase has a ΔTaq polymerase domain.

* * * * *

SEQUENCE LISTING

<160> NUMBER OF SEQ ID NOS: 36

<210> SEQ ID NO 1
<211> LENGTH: 189
<212> TYPE: DNA
<213> ORGANISM: Artificial Sequence
<220> FEATURE:
<223> OTHER INFORMATION: Description of Artificial Sequence:synthetic
      Sulfolobus solfataricus Sso7d gene

<400> SEQUENCE: 1
gcaaccgtaa agttcaagta caaaggcgaa gaaaaagagg tagacatctc caagatcaag      60
aaagtatggc gtgtgggcaa gatgatctcc ttcacctacg acgagggcgg tggcaagacc     120
ggccgtggtg cggtaagcga aaaggacgcg ccgaaggagc tgctgcagat gctggagaag     180
cagaaaaag                                                             189

<210> SEQ ID NO 2
<211> LENGTH: 63
<212> TYPE: PRT
<213> ORGANISM: Artificial Sequence
<220> FEATURE:
<223> OTHER INFORMATION: Description of Artificial Sequence:Sso7d

<400> SEQUENCE: 2

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 3
<211> LENGTH: 1899
<212> TYPE: DNA
<213> ORGANISM: Artificial Sequence
<220> FEATURE:
<223> OTHER INFORMATION: Description of Artificial Sequence:Sso7d-

-continued deltaTaq fusion protein

<400> SEQUENCE: 3

```
atgattacga attcgagcgc aaccgtaaag ttcaagtaca aaggcgaaga aaaagaggta     60
gacatctcca agatcaagaa agtatggcgt gtgggcaaga tgatctcctt cacctacgac    120
gagggcggtg gcaagaccgg ccgtggtgcg gtaagcgaaa aggacgcgcc gaaggagctg    180
ctgcagatgc tggagaagca gaaaaagggc ggcggtgtca ctagtcccaa ggccctggag    240
gaggccccct ggcccccgcc ggaaggggcc ttcgtgggct ttgtgctttc ccgcaaggag    300
cccatgtggg ccgatcttct ggccctggcc gccgccaggg ggggccgggt ccaccgggcc    360
cccgagcctt ataaagccct cagggacctg aaggaggcgc gggggcttct cgccaaagac    420
ctgagcgttc tggccctgag ggaaggcctt ggcctcccgc ccggcgacga ccccatgctc    480
ctcgcctacc tcctggaccc ttccaacacc acccccgagg gggtggcccg gcgctacggc    540
ggggagtgga cggaggaggc gggggagcgg gccgcccttt ccgagaggct cttcgccaac    600
ctgtggggga ggcttgaggg ggaggagagg ctcctttggc tttaccggga ggtggagagg    660
cccctttccg ctgtcctggc ccacatggag gccacggggg tgcgcctgga cgtggcctat    720
ctcagggcct tgtccctgga ggtggccgag gagatcgccc gcctcgaggc cgaggtcttc    780
cgcctggccg gccacccctt caacctcaac tcccgggacc agctggaaag ggtcctcttt    840
gacgagctag ggcttcccgc catcggcaag acggagaaga ccggcaagcg ctccaccagc    900
gccgccgtcc tggaggccct ccgcgaggcc caccccatcg tggagaagat cctgcagtac    960
cgggagctca ccaagctgaa gagcacctac attgacccct tgccggacct catccacccc   1020
aggacgggcc gcctccacac ccgcttcaac cagacggcca cggccacggg caggctaagt   1080
agctccgatc ccaacctcca gaacatcccc gtccgcaccc cgcttgggca gaggatccgc   1140
cgggccttca tcgccgagga ggggtggcta ttggtggccc tggactatag ccagatagag   1200
ctcagggtgc tggcccacct ctccggcgac gagaacctga tccgggtctt ccaggagggg   1260
cgggacatcc acacggagac cgccagctgg atgttcggcg tcccccggga ggccgtggac   1320
cccctgatgc gccgggcggc caagaccatc aacttcgggg tcctctacgg catgtcggcc   1380
caccgcctct cccaggagct agccatccct tacgaggagg cccaggcctt cattgagcgc   1440
tactttcaga gcttccccaa ggtgcgggcc tggattgaga agaccctgga ggagggcagg   1500
aggcgggggt acgtggagac cctcttcggc cgccgccgct acgtgccaga cctagaggcc   1560
cgggtgaaga gcgtgcggga ggcggccgag cgcatggcct tcaacatgcc cgtccagggc   1620
accgccgccg acctcatgaa gctggctatg gtgaagctct tccccaggct ggaggaaatg   1680
gggggccagga tgctccttca ggtccacgac gagctggtcc tcgaggcccc aaaagagagg   1740
gcggaggccg tggcccggct ggccaaggag gtcatggagg gggtgtatcc cctggccgtg   1800
cccctggagg tggaggtggg gataggggag gactggctct ccgccaagga gggcattgat   1860
ggccgcggcg gaggcgggca tcatcatcat catcattaa                          1899
```

<210> SEQ ID NO 4
<211> LENGTH: 632
<212> TYPE: PRT
<213> ORGANISM: Artificial Sequence
<220> FEATURE:
<223> OTHER INFORMATION: Description of Artificial Sequence:Sso7d-
      deltaTaq fusion protein

<400> SEQUENCE: 4

-continued

Met Ile Thr Asn Ser Ser Ala Thr Val Lys Phe Lys Tyr Lys Gly Glu
1 5 10 15

Glu Lys Glu Val Asp Ile Ser Lys Ile Lys Lys Val Trp Arg Val Gly
20 25 30

Lys Met Ile Ser Phe Thr Tyr Asp Glu Gly Gly Gly Lys Thr Gly Arg
35 40 45

Gly Ala Val Ser Glu Lys Asp Ala Pro Lys Glu Leu Leu Gln Met Leu
50 55 60

Glu Lys Gln Lys Lys Gly Gly Gly Val Thr Ser Pro Lys Ala Leu Glu
65 70 75 80

Glu Ala Pro Trp Pro Pro Pro Glu Gly Ala Phe Val Gly Phe Val Leu
85 90 95

Ser Arg Lys Glu Pro Met Trp Ala Asp Leu Leu Ala Leu Ala Ala Ala
100 105 110

Arg Gly Gly Arg Val His Arg Ala Pro Glu Pro Tyr Lys Ala Leu Arg
115 120 125

Asp Leu Lys Glu Ala Arg Gly Leu Leu Ala Lys Asp Leu Ser Val Leu
130 135 140

Ala Leu Arg Glu Gly Leu Gly Leu Pro Pro Gly Asp Asp Pro Met Leu
145 150 155 160

Leu Ala Tyr Leu Leu Asp Pro Ser Asn Thr Thr Pro Glu Gly Val Ala
165 170 175

Arg Arg Tyr Gly Gly Glu Trp Thr Glu Glu Ala Gly Glu Arg Ala Ala
180 185 190

Leu Ser Glu Arg Leu Phe Ala Asn Leu Trp Gly Arg Leu Glu Gly Glu
195 200 205

Glu Arg Leu Leu Trp Leu Tyr Arg Glu Val Glu Arg Pro Leu Ser Ala
210 215 220

Val Leu Ala His Met Glu Ala Thr Gly Val Arg Leu Asp Val Ala Tyr
225 230 235 240

Leu Arg Ala Leu Ser Leu Glu Val Ala Glu Glu Ile Ala Arg Leu Glu
245 250 255

Ala Glu Val Phe Arg Leu Ala Gly His Pro Phe Asn Leu Asn Ser Arg
260 265 270

Asp Gln Leu Glu Arg Val Leu Phe Asp Glu Leu Gly Leu Pro Ala Ile
275 280 285

Gly Lys Thr Glu Lys Thr Gly Lys Arg Ser Thr Ser Ala Ala Val Leu
290 295 300

Glu Ala Leu Arg Glu Ala His Pro Ile Val Glu Lys Ile Leu Gln Tyr
305 310 315 320

Arg Glu Leu Thr Lys Leu Lys Ser Thr Tyr Ile Asp Pro Leu Pro Asp
325 330 335

Leu Ile His Pro Arg Thr Gly Arg Leu His Thr Arg Phe Asn Gln Thr
340 345 350

Ala Thr Ala Thr Gly Arg Leu Ser Ser Ser Asp Pro Asn Leu Gln Asn
355 360 365

Ile Pro Val Arg Thr Pro Leu Gly Gln Arg Ile Arg Arg Ala Phe Ile
370 375 380

Ala Glu Glu Gly Trp Leu Leu Val Ala Leu Asp Tyr Ser Gln Ile Glu
385 390 395 400

Leu Arg Val Leu Ala His Leu Ser Gly Asp Glu Asn Leu Ile Arg Val
405 410 415

Phe Gln Glu Gly Arg Asp Ile His Thr Glu Thr Ala Ser Trp Met Phe

```
            420                 425                 430

Gly Val Pro Arg Glu Ala Val Asp Pro Leu Met Arg Arg Ala Ala Lys
        435                 440                 445

Thr Ile Asn Phe Gly Val Leu Tyr Gly Met Ser Ala His Arg Leu Ser
    450                 455                 460

Gln Glu Leu Ala Ile Pro Tyr Glu Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Arg Gly Tyr Val Glu Thr Leu Phe Gly Arg Arg
            500                 505                 510

Arg Tyr Val Pro Asp Leu Glu Ala Arg Val Lys Ser Val Arg Glu Ala
        515                 520                 525

Ala Glu Arg Met Ala Phe Asn Met Pro Val Gln Gly Thr Ala Ala Asp
    530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
            580                 585                 590

Glu Gly Val Tyr Pro Leu Ala Val Pro Leu Glu Val Glu Val Gly Ile
        595                 600                 605

Gly Glu Asp Trp Leu Ser Ala Lys Glu Gly Ile Asp Gly Arg Gly Gly
    610                 615                 620

Gly Gly His His His His His His
625                 630


<210> SEQ ID NO 5
<211> LENGTH: 2763
<212> TYPE: DNA
<213> ORGANISM: Artificial Sequence
<220> FEATURE:
<223> OTHER INFORMATION: Description of Artificial Sequence:Sso7d-Taq
      fusion protein, Sso7d/full-length Taq fusion
      protein

<400> SEQUENCE: 5

atgattacga attcgagcgc aaccgtaaag ttcaagtaca aaggcgaaga aaaagaggta      60

gacatctcca agatcaagaa agtatggcgt gtgggcaaga tgatctcctt cacctacgac     120

gagggcggtg gcaagaccgg ccgtggtgcg gtaagcgaaa aggacgcgcc gaaggagctg     180

ctgcagatgc tggagaagca gaaaaagggc ggcggtgtca ctagtgggat gctgcccctc     240

tttgagccca agggccgggt cctcctggtg gacggccacc acctggccta ccgcaccttc     300

cacgccctga agggcctcac caccagccgg ggggagccgg tgcaggcggt ctacggcttc     360

gccaagagcc tcctcaaggc cctcaaggag gacggggacg cggtgatcgt ggtctttgac     420

gccaaggccc cctccttccg ccacgaggcc tacggggggt acaaggcggg ccgggccccc     480

acgccagagg actttccccg gcaactcgcc ctcatcaagg agctggtgga cctcctgggg     540

ctggcgcgcc tcgaggtccc gggctacgag gcggacgacg tcctggccag cctggccaag     600

aaggcggaaa aggagggcta cgaggtccgc atcctcaccg ccgacaaaga cctttaccag     660

ctcctttccg accgcatcca cgtcctccac cccgaggggt acctcatcac cccggcctgg     720

ctttgggaaa agtacggcct gaggcccgac cagtgggccg actaccgggc cctgaccggg     780
```

-continued

```
gacgagtccg acaaccttcc cggggtcaag ggcatcgggg agaagacggc gaggaagctt     840
ctggaggagt gggggagcct ggaagccctc ctcaagaacc tggaccggct gaagcccgcc     900
atccgggaga agatcctggc ccacatggac gatctgaagc tctcctggga cctggccaag     960
gtgcgcaccg acctgcccct ggaggtggac ttcgccaaaa ggcgggagcc cgaccgggag    1020
aggcttaggg cctttctgga gaggcttgag tttggcagcc tcctccacga gttcggcctt    1080
ctggaaagcc ccaaggccct ggaggaggcc ccctggcccc cgccggaagg ggccttcgtg    1140
ggctttgtgc tttcccgcaa ggagcccatg tgggccgatc ttctggccct ggccgccgcc    1200
aggggggggcc gggtccaccg ggcccccgag ccttataaag ccctcaggga cctgaaggag    1260
gcgcgggggc ttctcgccaa agacctgagc gttctggccc tgagggaagg ccttggcctc    1320
ccgcccggcg acgaccccat gctcctcgcc tacctcctgg acccttccaa caccaccccc    1380
gagggggtgg cccggcgcta cggcggggag tggacggagg aggcggggga gcgggccgcc    1440
ctttccgaga ggctcttcgc caacctgtgg gggaggcttg agggggagga gaggctcctt    1500
tggctttacc gggaggtgga gaggcccctt tccgctgtcc tggcccacat ggaggccacg    1560
ggggtgcgcc tggacgtggc ctatctcagg gccttgtccc tggaggtggc cgaggagatc    1620
gcccgcctcg aggccgaggt cttccgcctg gccggccacc ccttcaacct caactcccgg    1680
gaccagctgg aaagggtcct ctttgacgag ctagggcttc ccgccatcgg caagacggag    1740
aagaccggca agcgctccac cagcgccgcc gtcctggagg ccctccgcga ggcccacccc    1800
atcgtggaga agatcctgca gtaccgggag ctcaccaagc tgaagagcac ctacattgac    1860
cccttgccgg acctcatcca ccccaggacg ggccgcctcc acacccgctt caaccagacg    1920
gccacggcca cgggcaggct aagtagctcc gatcccaacc tccagaacat ccccgtccgc    1980
accccgcttg ggcagaggat ccgccgggcc ttcatcgccg aggaggggtg gctattggtg    2040
gccctggact atagccagat agagctcagg gtgctggccc acctctccgg cgacgagaac    2100
ctgatccggg tcttccagga ggggcgggac atccacacgg agaccgccag ctggatgttc    2160
ggcgtccccc gggaggccgt ggacccccctg atgcgccggg cggccaagac catcaacttc    2220
ggggtcctct acggcatgtc ggcccaccgc ctctcccagg agctagccat cccttacgag    2280
gaggcccagg ccttcattga gcgctacttt cagagcttcc ccaaggtgcg ggcctggatt    2340
gagaagaccc tggaggaggg caggaggcgg gggtacgtgg agaccctctt cggccgccgc    2400
cgctacgtgc cagacctaga ggcccgggtg aagagcgtgc gggaggcggc cgagcgcatg    2460
gccttcaaca tgcccgtcca gggcaccgcc gccgacctca tgaagctggc tatggtgaag    2520
ctcttcccca ggctggagga aatgggggcc aggatgctcc ttcaggtcca cgacgagctg    2580
gtcctcgagg ccccaaaaga gagggcggag gccgtggccc ggctggccaa ggaggtcatg    2640
gagggggtgt atcccctggc cgtgcccctg gaggtggagg tggggatagg ggaggactgg    2700
ctctccgcca aggagggcat tgatggccgc ggcggaggcg ggcatcatca tcatcatcat    2760
taa                                                                  2763
```

<210> SEQ ID NO 6
<211> LENGTH: 920
<212> TYPE: PRT
<213> ORGANISM: Artificial Sequence
<220> FEATURE:
<223> OTHER INFORMATION: Description of Artificial Sequence:Sso7d-Taq fusion protein, Sso7d/full-length Taq fusion protein

<400> SEQUENCE: 6

-continued

```
Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Gly Lys Thr Gly Arg
        35                  40                  45

Gly Ala Val Ser Glu Lys Asp Ala Pro Lys Glu Leu Leu Gln Met Leu
    50                  55                  60

Glu Lys Gln Lys Lys Gly Gly Gly Val Thr Ser Gly Met Leu Pro Leu
65                  70                  75                  80

Phe Glu Pro Lys Gly Arg Val Leu Leu Val Asp Gly His His Leu Ala
                85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
        115                 120                 125

Lys Glu Asp Gly Asp Ala Val Ile Val Val Phe Asp Ala Lys Ala Pro
    130                 135                 140

Ser Phe Arg His Glu Ala Tyr Gly Gly Tyr Lys Ala Gly Arg Ala Pro
145                 150                 155                 160

Thr Pro Glu Asp Phe Pro Arg Gln Leu Ala Leu Ile Lys Glu Leu Val
                165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
        195                 200                 205

Val Arg Ile Leu Thr Ala Asp Lys Asp Leu Tyr Gln Leu Leu Ser Asp
    210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
                245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
        275                 280                 285

Ala Leu Leu Lys Asn Leu Asp Arg Leu Lys Pro Ala Ile Arg Glu Lys
    290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
                325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
        355                 360                 365

Glu Ala Pro Trp Pro Pro Pro Glu Gly Ala Phe Val Gly Phe Val Leu
    370                 375                 380

Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
                405                 410                 415
```

-continued

```
Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
        435                 440                 445

Leu Ala Tyr Leu Leu Asp Pro Ser Asn Thr Thr Pro Glu Gly Val Ala
    450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu
                485                 490                 495

Glu Arg Leu Leu Trp Leu Tyr Arg Glu Val Glu Arg Pro Leu Ser Ala
            500                 505                 510

Val Leu Ala His Met Glu Ala Thr Gly Val Arg Leu Asp Val Ala Tyr
        515                 520                 525

Leu Arg Ala Leu Ser Leu Glu Val Ala Glu Glu Ile Ala Arg Leu Glu
    530                 535                 540

Ala Glu Val Phe Arg Leu Ala Gly His Pro Phe Asn Leu Asn Ser Arg
545                 550                 555                 560

Asp Gln Leu Glu Arg Val Leu Phe Asp Glu Leu Gly Leu Pro Ala Ile
                565                 570                 575

Gly Lys Thr Glu Lys Thr Gly Lys Arg Ser Thr Ser Ala Ala Val Leu
            580                 585                 590

Glu Ala Leu Arg Glu Ala His Pro Ile Val Glu Lys Ile Leu Gln Tyr
        595                 600                 605

Arg Glu Leu Thr Lys Leu Lys Ser Thr Tyr Ile Asp Pro Leu Pro Asp
    610                 615                 620

Leu Ile His Pro Arg Thr Gly Arg Leu His Thr Arg Phe Asn Gln Thr
625                 630                 635                 640

Ala Thr Ala Thr Gly Arg Leu Ser Ser Ser Asp Pro Asn Leu Gln Asn
                645                 650                 655

Ile Pro Val Arg Thr Pro Leu Gly Gln Arg Ile Arg Arg Ala Phe Ile
            660                 665                 670

Ala Glu Glu Gly Trp Leu Leu Val Ala Leu Asp Tyr Ser Gln Ile Glu
        675                 680                 685

Leu Arg Val Leu Ala His Leu Ser Gly Asp Glu Asn Leu Ile Arg Val
    690                 695                 700

Phe Gln Glu Gly Arg Asp Ile His Thr Glu Thr Ala Ser Trp Met Phe
705                 710                 715                 720

Gly Val Pro Arg Glu Ala Val Asp Pro Leu Met Arg Arg Ala Ala Lys
                725                 730                 735

Thr Ile Asn Phe Gly Val Leu Tyr Gly Met Ser Ala His Arg Leu Ser
            740                 745                 750

Gln Glu Leu Ala Ile Pro Tyr Glu Glu Ala Gln Ala Phe Ile Glu Arg
        755                 760                 765

Tyr Phe Gln Ser Phe Pro Lys Val Arg Ala Trp Ile Glu Lys Thr Leu
    770                 775                 780

Glu Glu Gly Arg Arg Arg Gly Tyr Val Glu Thr Leu Phe Gly Arg Arg
785                 790                 795                 800

Arg Tyr Val Pro Asp Leu Glu Ala Arg Val Lys Ser Val Arg Glu Ala
                805                 810                 815

Ala Glu Arg Met Ala Phe Asn Met Pro Val Gln Gly Thr Ala Ala Asp
            820                 825                 830

Leu Met Lys Leu Ala Met Val Lys Leu Phe Pro Arg Leu Glu Glu Met
```

-continued

```
        835                 840                 845

Gly Ala Arg Met Leu Leu Gln Val His Asp Glu Leu Val Leu Glu Ala
    850                 855                 860

Pro Lys Glu Arg Ala Glu Ala Val Ala Arg Leu Ala Lys Glu Val Met
865                 870                 875                 880

Glu Gly Val Tyr Pro Leu Ala Val Pro Leu Glu Val Glu Val Gly Ile
                885                 890                 895

Gly Glu Asp Trp Leu Ser Ala Lys Glu Gly Ile Asp Gly Arg Gly Gly
            900                 905                 910

Gly Gly His His His His His His
        915                 920
```

<210> SEQ ID NO 7
<211> LENGTH: 2535
<212> TYPE: DNA
<213> ORGANISM: Artificial Sequence
<220> FEATURE:
<223> OTHER INFORMATION: Description of Artificial Sequence:Pfu-Sso7d fusion protein

<400> SEQUENCE: 7

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga    180

aagattgtga gaattgttga tgtagagaag gttgagaaaa agtttctcgg caagcctatt    240

accgtgtgga aactttattt ggaacatccc caagatgttc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgacttccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg ggaagaaag    1560
```

```
tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca ttgagaacca ggttcttcca   2220

gcggtactta ggatattgga gggatttgga tacagaaagg aagacctcag ataccaaaag   2280

acaagacaag tcggcctaac ttcctggctt aacattaaaa aatccggtac cggcggtggc   2340

ggtgcaaccg taaagttcaa gtacaaaggc gaagaaaaag aggtagacat ctccaagatc   2400

aagaaagtat ggcgtgtggg caagatgatc tccttcacct acgacgaggg cggtggcaag   2460

accggccgtg gtgcggtaag cgaaaaggac gcgccgaagg agctgctgca gatgctggag   2520

aagcagaaaa agtga                                                    2535
```

<210> SEQ ID NO 8
<211> LENGTH: 844
<212> TYPE: PRT
<213> ORGANISM: Artificial Sequence
<220> FEATURE:
<223> OTHER INFORMATION: Description of Artificial Sequence:Pfu-Sso7d fusion protein

<400> SEQUENCE: 8

```
Met Ile Leu Asp Val Asp Tyr Ile Thr Glu Glu Gly Lys Pro Val Ile
  1               5                  10                  15

Arg Leu Phe Lys Lys Glu Asn Gly Lys Phe Lys Ile Glu His Asp Arg
             20                  25                  30

Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
     50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175
```

-continued

```
Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
```

-continued

```
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser Gly Thr Gly Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840


<210> SEQ ID NO 9
<211> LENGTH: 1904
<212> TYPE: DNA
<213> ORGANISM: Artificial Sequence
<220> FEATURE:
<223> OTHER INFORMATION: Description of Artificial Sequence:Sac7d-
      deltaTaq fusion protein

<400> SEQUENCE: 9

atgattacga attcgacggt gaaggtaaag ttcaagtata agggtgaaga gaaagaagta      60

gacacttcaa agataaagaa ggtttggaga gtaggcaaaa tggtgtcctt tacctatgac     120

gacaatggta agacaggtag aggagctgta agcgagaaag atgctccaaa agaattatta     180

gacatgttag caagagcaga aagagagaag aaaggcggcg gtgtcactag tcccaaggcc     240

ctggaggagg ccccctggcc cccgccggaa ggggccttcg tgggctttgt gctttcccgc     300

aaggagccca tgtgggccga tcttctggcc ctggccgccg ccaggggggg ccgggtccac     360

cgggcccccg agccttataa agccctcagg gacctgaagg aggcgcgggg gcttctcgcc     420

aaagacctga gcgttctggc cctgagggaa ggccttggcc tcccgcccgg cgacgacccc     480

atgctcctcg cctacctcct ggacccttcc aacaccaccc ccgagggggt ggcccggcgc     540

tacggcgggg agtggacgga ggaggcgggg gagcgggccg ccctttccga gaggctcttc     600

gccaacctgt gggggaggct tgagggggag gagaggctcc tttggcttta ccgggaggtg     660
```

```
gagaggcccc tttccgctgt cctggcccac atggaggcca cgggggtgcg cctggacgtg    720

gcctatctca gggccttgtc cctggaggtg gccgaggaga tcgcccgcct cgaggccggg    780

tcttccgcct ggccggccac cccttcaacc tcaactcccg ggaccagctg gaaagggtcc    840

tctttgacga gctagggctt cccgccatcg gcaagacgga gaagaccggc aagcgctcca    900

ccagcgccgc cgtcctggag gccctccgcg aggcccaccc catcgtggag aagatcctgc    960

agtaccggga gctcaccaag ctgaagagca cctacattga ccccttgccg gacctcatcc   1020

accccaggac gggccgcctc cacacccgct tcaaccagac ggccacggcc acgggcaggc   1080

taagtagctc cgatcccaac ctccagaaca tccccgtccg caccccgctt gggcagagga   1140

tccgccgggc cttcatcgcc gaggaggggt ggctattggt ggccctggac tatagccaga   1200

tagagctcag ggtgctggcc cacctctccg gcgacgagaa cctgatccgg gtcttccagg   1260

aggggcggga catccacacg gagaccgcca gctggatgtt cggcgtcccc cgggaggccg   1320

tggacccccct gatgcgccgg gcggccaaga ccatcaactt cggggtcctc tacggcatgt   1380

cggcccaccg cctctcccag gagctagcca tcccttacga ggaggcccag gccttcattg   1440

agcgctactt tcagagcttc cccaaggtgc gggcctggat tgagaagacc ctggaggagg   1500

gcaggaggcg gggtacgtg gagaccctct tcggccgccg ccgctacgtg ccagacctag   1560

aggcccgggt gaagagcgtg cgggaggcgg ccgagcgcat ggccttcaac atgcccgtcc   1620

agggcaccgc cgccgacctc atgaagctgg ctatggtgaa gctcttcccc aggctggagg   1680

aaatgggggc caggatgctc cttcaggtcc acgacgagct ggtcctcgag gccccaaaag   1740

agagggcgga ggccgtggcc cggctggcca aggaggtcat ggagggggtg tatcccctgg   1800

ccgtgcccct ggaggtggag gtggggatag gggaggactg gctctccgcc aaggagggca   1860

ttgatggccg cggcggaggc gggcatcatc atcatcatca ttaa                    1904
```

```
<210> SEQ ID NO 10
<211> LENGTH: 634
<212> TYPE: PRT
<213> ORGANISM: Artificial Sequence
<220> FEATURE:
<223> OTHER INFORMATION: Description of Artificial Sequence:Sac7d-
      deltaTaq fusion protein

<400> SEQUENCE: 10

Met Ile Thr Asn Ser Thr Val Lys Val Lys Phe Lys Tyr Lys Gly Glu
1               5                   10                  15

Glu Lys Glu Val Asp Thr Ser Lys Ile Lys Lys Val Trp Arg Val Gly
            20                  25                  30

Lys Met Val Ser Phe Thr Tyr Asp Asp Asn Gly Lys Thr Gly Arg Gly
        35                  40                  45

Ala Val Ser Glu Lys Asp Ala Pro Lys Glu Leu Leu Asp Met Leu Ala
    50                  55                  60

Arg Ala Glu Arg Glu Lys Lys Gly Gly Gly Val Thr Ser Pro Lys Ala
65                  70                  75                  80

Leu Glu Glu Ala Pro Trp Pro Pro Pro Glu Gly Ala Phe Val Gly Phe
                85                  90                  95

Val Leu Ser Arg Lys Glu Pro Met Trp Ala Asp Leu Leu Ala Leu Ala
            100                 105                 110

Ala Ala Arg Gly Gly Arg Val His Arg Ala Pro Glu Pro Tyr Lys Ala
        115                 120                 125

Leu Arg Asp Leu Lys Glu Ala Arg Gly Leu Leu Ala Lys Asp Leu Ser
```

-continued

```
    130                 135                 140

Val Leu Ala Leu Arg Glu Gly Leu Gly Leu Pro Pro Gly Asp Asp Pro
145                 150                 155                 160

Met Leu Leu Ala Tyr Leu Leu Asp Pro Ser Asn Thr Thr Pro Glu Gly
                165                 170                 175

Val Ala Arg Arg Tyr Gly Gly Glu Trp Thr Glu Glu Ala Gly Glu Arg
            180                 185                 190

Ala Ala Leu Ser Glu Arg Leu Phe Ala Asn Leu Trp Gly Arg Leu Glu
        195                 200                 205

Gly Glu Glu Arg Leu Leu Trp Leu Tyr Arg Glu Val Glu Arg Pro Leu
    210                 215                 220

Ser Ala Val Leu Ala His Met Glu Ala Thr Gly Val Arg Leu Asp Val
225                 230                 235                 240

Ala Tyr Leu Arg Ala Leu Ser Leu Glu Val Ala Glu Glu Ile Ala Arg
                245                 250                 255

Leu Glu Ala Glu Val Phe Arg Leu Ala Gly His Pro Phe Asn Leu Asn
            260                 265                 270

Ser Arg Asp Gln Leu Glu Arg Val Leu Phe Asp Glu Leu Gly Leu Pro
        275                 280                 285

Ala Ile Gly Lys Thr Glu Lys Thr Gly Lys Arg Ser Thr Ser Ala Ala
    290                 295                 300

Val Leu Glu Ala Leu Arg Glu Ala His Pro Ile Val Glu Lys Ile Leu
305                 310                 315                 320

Gln Tyr Arg Glu Leu Thr Lys Leu Lys Ser Thr Tyr Ile Asp Pro Leu
                325                 330                 335

Pro Asp Leu Ile His Pro Arg Thr Gly Arg Leu His Thr Arg Phe Asn
            340                 345                 350

Gln Thr Ala Thr Ala Thr Gly Arg Leu Ser Ser Ser Asp Pro Asn Leu
        355                 360                 365

Gln Asn Ile Pro Val Arg Thr Pro Leu Gly Gln Arg Ile Arg Arg Ala
    370                 375                 380

Phe Ile Ala Glu Glu Gly Trp Leu Leu Val Ala Leu Asp Tyr Ser Gln
385                 390                 395                 400

Ile Glu Leu Arg Val Leu Ala His Leu Ser Gly Asp Glu Asn Leu Ile
                405                 410                 415

Arg Val Phe Gln Glu Gly Arg Asp Ile His Thr Glu Thr Ala Ser Trp
            420                 425                 430

Met Phe Gly Val Pro Arg Glu Ala Val Asp Pro Leu Met Arg Arg Ala
        435                 440                 445

Ala Lys Thr Ile Asn Phe Gly Val Leu Tyr Gly Met Ser Ala His Arg
    450                 455                 460

Leu Ser Gln Glu Leu Ala Ile Pro Tyr Glu Glu Ala Gln Ala Phe Ile
465                 470                 475                 480

Glu Arg Tyr Phe Gln Ser Phe Pro Lys Val Arg Ala Trp Ile Glu Lys
                485                 490                 495

Thr Leu Glu Glu Gly Arg Arg Arg Gly Tyr Val Glu Thr Leu Phe Gly
            500                 505                 510

Arg Arg Arg Tyr Val Pro Asp Leu Glu Ala Arg Val Lys Ser Val Arg
        515                 520                 525

Glu Ala Ala Glu Arg Met Ala Phe Asn Met Pro Val Gln Gly Thr Ala
    530                 535                 540

Ala Asp Leu Met Lys Leu Ala Met Val Lys Leu Phe Pro Arg Leu Glu
545                 550                 555                 560
```

```
Glu Met Gly Ala Arg Met Leu Leu Gln Val His Asp Glu Leu Val Leu
                565                 570                 575

Glu Ala Pro Lys Glu Arg Ala Glu Ala Val Ala Arg Leu Ala Lys Glu
            580                 585                 590

Val Met Glu Gly Val Tyr Pro Leu Ala Val Pro Leu Glu Val Glu Val
        595                 600                 605

Gly Ile Gly Glu Asp Trp Leu Ser Ala Lys Glu Gly Ile Asp Gly Arg
    610                 615                 620

Gly Gly Gly Gly His His His His His His
625                 630


<210> SEQ ID NO 11
<211> LENGTH: 1965
<212> TYPE: DNA
<213> ORGANISM: Artificial Sequence
<220> FEATURE:
<223> OTHER INFORMATION: Description of Artificial Sequence:polylysine
      (PL)-deltaTaq fusion protein

<400> SEQUENCE: 11

atgattacga attcgaagaa aaagaaaaag aaaaagcgta agaaacgcaa aaagaaaaag     60

aaaggcggcg gtgtcactag tggcgcaacc gtaaagttca agtacaaagg cgaagaaaaa    120

gaggtagaca tctccaagat caagaaagta tggcgtgtgg gcaagatgat ctccttcacc    180

tacgacgagg gcggtggcaa gaccggccgt ggtgcggtaa gcgaaaagga cgcgccgaag    240

gagctgctgc agatgctgga gaagcagaaa aagggcggcg gtgtcaccag tcccaaggcc    300

ctggaggagg ccccctggcc cccgccggaa ggggccttcg tgggctttgt gctttcccgc    360

aaggagccca tgtgggccga tcttctggcc ctggccgccg ccaggggggg ccgggtccac    420

cgggcccccg agccttataa agccctcagg gacctgaagg aggcgcgggg gcttctcgcc    480

aaagacctga gcgttctggc cctgagggaa ggccttggcc tcccgcccgg cgacgacccc    540

atgctcctcg cctacctcct ggacccttcc aacaccaccc ccgagggggt ggcccggcgc    600

tacggcgggg agtggacgga ggaggcgggg gagcgggccg ccctttccga gaggctcttc    660

gccaacctgt gggggaggct tgagggggag gagaggctcc tttggcttta ccgggaggtg    720

gagaggcccc tttccgctgt cctggcccac atggaggcca cgggggtgcg cctggacgtg    780

gcctatctca gggccttgtc cctggaggtg gccgaggaga tcgcccgcct cgaggccgag    840

gtcttccgcc tggccggcca ccccttcaac ctcaactccc gggaccagct ggaaagggtc    900

ctctttgacg agctagggct tcccgccatc ggcaagacgg agaagaccgg caagcgctcc    960

accagcgccg ccgtcctgga ggccctccgc gaggcccacc ccatcgtgga gaagatcctg   1020

cagtaccggg agctcaccaa gctgaagagc acctacattg accccttgcc ggacctcatc   1080

caccccagga cgggccgcct ccacacccgc ttcaaccaga cggccacggc cacgggcagg   1140

ctaagtagct ccgatcccaa cctccagaac atccccgtcc gcaccccgct tgggcagagg   1200

atccgccggg ccttcatcgc cgaggagggg tggctattgg tggccctgga ctatagccag   1260

atagagctca gggtgctggc ccacctctcc ggcgacgaga acctgatccg ggtcttccag   1320

gaggggcggg acatccacac ggagaccgcc agctggatgt tcggcgtccc ccgggaggcc   1380

gtggaccccc tgatgcgccg ggcggccaag accatcaact tcggggtcct ctacggcatg   1440

tcggcccacc gcctctccca ggagctagcc atcccttacg aggaggccca ggccttcatt   1500

gagcgctact ttcagagctt ccccaaggtg cgggcctgga ttgagaagac cctggaggag   1560
```

-continued ggcaggaggc gggggtacgt ggagaccctc ttcggccgcc gccgctacgt gccagaccta 1620
gaggcccggg tgaagagcgt gcgggaggcg gccgagcgca tggccttcaa catgcccgtc 1680
cagggcaccg ccgccgacct catgaagctg gctatggtga agctcttccc caggctggag 1740
gaaatggggg ccaggatgct ccttcaggtc cacgacgagc tggtcctcga ggccccaaaa 1800
gagagggcgg aggccgtggc ccggctggcc aaggaggtca tggagggggt gtatcccctg 1860
gccgtgcccc tggaggtgga ggtggggata ggggaggact ggctctccgc caaggagggc 1920
attgatggcc gcggcggagg cgggcatcat catcatcatc attaa 1965

<210> SEQ ID NO 12
<211> LENGTH: 654
<212> TYPE: PRT
<213> ORGANISM: Artificial Sequence
<220> FEATURE:
<223> OTHER INFORMATION: Description of Artificial Sequence:polylysine (PL)-deltaTaq fusion protein

<400> SEQUENCE: 12

Met Ile Thr Asn Ser Lys Lys Lys Lys Lys Lys Lys Arg Lys Lys Arg
1 5 10 15

Lys Lys Lys Lys Lys Gly Gly Gly Val Thr Ser Gly Ala Thr Val Lys
20 25 30

Phe Lys Tyr Lys Gly Glu Glu Lys Glu Val Asp Ile Ser Lys Ile Lys
35 40 45

Lys Val Trp Arg Val Gly Lys Met Ile Ser Phe Thr Tyr Asp Glu Gly
50 55 60

Gly Gly Lys Thr Gly Arg Gly Ala Val Ser Glu Lys Asp Ala Pro Lys
65 70 75 80

Glu Leu Leu Gln Met Leu Glu Lys Gln Lys Lys Gly Gly Gly Val Thr
85 90 95

Ser Pro Lys Ala Leu Glu Glu Ala Pro Trp Pro Pro Pro Glu Gly Ala
100 105 110

Phe Val Gly Phe Val Leu Ser Arg Lys Glu Pro Met Trp Ala Asp Leu
115 120 125

Leu Ala Leu Ala Ala Ala Arg Gly Gly Arg Val His Arg Ala Pro Glu
130 135 140

Pro Tyr Lys Ala Leu Arg Asp Leu Lys Glu Ala Arg Gly Leu Leu Ala
145 150 155 160

Lys Asp Leu Ser Val Leu Ala Leu Arg Glu Gly Leu Gly Leu Pro Pro
165 170 175

Gly Asp Asp Pro Met Leu Leu Ala Tyr Leu Leu Asp Pro Ser Asn Thr
180 185 190

Thr Pro Glu Gly Val Ala Arg Arg Tyr Gly Gly Glu Trp Thr Glu Glu
195 200 205

Ala Gly Glu Arg Ala Ala Leu Ser Glu Arg Leu Phe Ala Asn Leu Trp
210 215 220

Gly Arg Leu Glu Gly Glu Glu Arg Leu Leu Trp Leu Tyr Arg Glu Val
225 230 235 240

Glu Arg Pro Leu Ser Ala Val Leu Ala His Met Glu Ala Thr Gly Val
245 250 255

Arg Leu Asp Val Ala Tyr Leu Arg Ala Leu Ser Leu Glu Val Ala Glu
260 265 270

Glu Ile Ala Arg Leu Glu Ala Glu Val Phe Arg Leu Ala Gly His Pro
275 280 285

-continued

```
Phe Asn Leu Asn Ser Arg Asp Gln Leu Glu Arg Val Leu Phe Asp Glu
    290                 295                 300

Leu Gly Leu Pro Ala Ile Gly Lys Thr Glu Lys Thr Gly Lys Arg Ser
305                 310                 315                 320

Thr Ser Ala Ala Val Leu Glu Ala Leu Arg Glu Ala His Pro Ile Val
                325                 330                 335

Glu Lys Ile Leu Gln Tyr Arg Glu Leu Thr Lys Leu Lys Ser Thr Tyr
            340                 345                 350

Ile Asp Pro Leu Pro Asp Leu Ile His Pro Arg Thr Gly Arg Leu His
        355                 360                 365

Thr Arg Phe Asn Gln Thr Ala Thr Ala Thr Gly Arg Leu Ser Ser Ser
    370                 375                 380

Asp Pro Asn Leu Gln Asn Ile Pro Val Arg Thr Pro Leu Gly Gln Arg
385                 390                 395                 400

Ile Arg Arg Ala Phe Ile Ala Glu Glu Gly Trp Leu Leu Val Ala Leu
                405                 410                 415

Asp Tyr Ser Gln Ile Glu Leu Arg Val Leu Ala His Leu Ser Gly Asp
            420                 425                 430

Glu Asn Leu Ile Arg Val Phe Gln Glu Gly Arg Asp Ile His Thr Glu
        435                 440                 445

Thr Ala Ser Trp Met Phe Gly Val Pro Arg Glu Ala Val Asp Pro Leu
    450                 455                 460

Met Arg Arg Ala Ala Lys Thr Ile Asn Phe Gly Val Leu Tyr Gly Met
465                 470                 475                 480

Ser Ala His Arg Leu Ser Gln Glu Leu Ala Ile Pro Tyr Glu Glu Ala
                485                 490                 495

Gln Ala Phe Ile Glu Arg Tyr Phe Gln Ser Phe Pro Lys Val Arg Ala
            500                 505                 510

Trp Ile Glu Lys Thr Leu Glu Glu Gly Arg Arg Arg Gly Tyr Val Glu
        515                 520                 525

Thr Leu Phe Gly Arg Arg Arg Tyr Val Pro Asp Leu Glu Ala Arg Val
    530                 535                 540

Lys Ser Val Arg Glu Ala Ala Glu Arg Met Ala Phe Asn Met Pro Val
545                 550                 555                 560

Gln Gly Thr Ala Ala Asp Leu Met Lys Leu Ala Met Val Lys Leu Phe
                565                 570                 575

Pro Arg Leu Glu Glu Met Gly Ala Arg Met Leu Leu Gln Val His Asp
            580                 585                 590

Glu Leu Val Leu Glu Ala Pro Lys Glu Arg Ala Glu Ala Val Ala Arg
        595                 600                 605

Leu Ala Lys Glu Val Met Glu Gly Val Tyr Pro Leu Ala Val Pro Leu
    610                 615                 620

Glu Val Glu Val Gly Ile Gly Glu Asp Trp Leu Ser Ala Lys Glu Gly
625                 630                 635                 640

Ile Asp Gly Arg Gly Gly Gly Gly His His His His His His
                645                 650
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer L71F

<400> SEQUENCE: 13

-continued

```
cctgctctgc cgcttcacgc                                                 20


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer L71R

<400> SEQUENCE: 14

gcacagcggc tggctgagga                                                 20


<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:primer
      L18015F

<400> SEQUENCE: 15

tgacggagga taacgccagc ag                                              22


<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:primer
      L23474F

<400> SEQUENCE: 16

gaaagacgat gggtcgctaa tacgc                                           25


<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:primer
      L18015F

<400> SEQUENCE: 17

tgacggagga taacgccagc ag                                              22


<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:primer
      L29930R

<400> SEQUENCE: 18

ggggttggag gtcaatgggt tc                                              22


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:primer
      L30350F

<400> SEQUENCE: 19

cctgctctgc cgcttcacgc                                                 20
```

-continued

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:primer
L35121R

<400> SEQUENCE: 20
cacatggtac agcaagcctg gc 22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:primer
L2089F

<400> SEQUENCE: 21
cccgtatctg ctgggatact ggc 23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:primer
L7112R

<400> SEQUENCE: 22
cagcggtgct gactgaatca tgg 23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:primer
L30350F

<400> SEQUENCE: 23
cctgcctgcc gcttcacgc 19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:primer
L40547R

<400> SEQUENCE: 24
ccaatacccg tttcatcgcg gc 22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:primer
H-Amelo-Y

<400> SEQUENCE: 25
ccacctcatc ctgggcacc 19

-continued

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:primer
H-Amelo-YR

<400> SEQUENCE: 26
gcttgaggcc aaccatcaga gc 22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:human
beta-globin primer 536F

<400> SEQUENCE: 27
ggttggccaa tctactccca gg 22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:human
beta-globin primer 536R

<400> SEQUENCE: 28
gctcactcag tgtggcaaag 20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:human
beta-globin primer 1408R

<400> SEQUENCE: 29
gattagcaaa agggcctagc ttgg 24

<210> SEQ ID NO 30
<211> LENGTH: 1899
<212> TYPE: DNA
<213> ORGANISM: Artificial Sequence
<220> FEATURE:
<223> OTHER INFORMATION: Description of Artificial
Sequence:Sso7d-deltaTaq(Y) fusion protein

<400> SEQUENCE: 30
atgattacga attcgagcgc aaccgtaaag ttcaagtaca aaggcgaaga aaaagaggta 60
gacatctcca agatcaagaa agtatggcgt gtgggcaaga tgatctcctt cacctacgac 120
gagggcggtg gcaagaccgg ccgtggtgcg gtaagcgaaa aggacgcgcc gaaggagctg 180
ctgcagatgc tggagaagca gaaaaagggc ggcggtgtca ctagtcccaa ggccctggag 240
gaggccccct ggcccccgcc ggaaggggcc ttcgtgggct ttgtgctttc ccgcaaggag 300
cccatgtggg ccgatcttct ggccctggcc gccgccaggg ggggccgggt ccaccgggcc 360
cccgagcctt ataaagccct cagggacctg aaggaggcgc gggggcttct cgccaaagac 420
ctgagcgttc tggccctgag ggaaggcctt ggcctcccgc ccggcgacga ccccatgctc 480
ctcgcctacc tcctggaccc ttccaacacc acccccgagg gggtggcccg gcgctacggc 540

-continued

```
ggggagtgga cggaggaggc gggggagcgg gccgcccttt ccgagaggct cttcgccaac    600

ctgtggggga ggcttgaggg ggaggagagg ctcctttggc tttaccggga ggtggagagg    660

ccccttttccg ctgtcctggc ccacatggag gccacggggg tgcgcctgga cgtggcctat    720

ctcagggcct tgtccctgga ggtggccgag gagatcgccc gcctcgaggc cgaggtcttc    780

cgcctggccg gccacccctt caacctcaac tcccgggacc agctggaaag ggtcctcttt    840

gacgagctag ggcttcccgc catcggcaag acggagaaga ccggcaagcg ctccaccagc    900

gccgccgtcc tggaggccct ccgcgaggcc caccccatcg tggagaagat cctgcagtac    960

cgggagctca ccaagctgaa gagcacctac attgacccct tgccggacct catccacccc   1020

aggacgggcc gcctccacac ccgcttcaac cagacggcca cggccacggg caggctaagt   1080

agctccgatc ccaacctcca gaacatcccc gtccgcaccc cgcttgggca gaggatccgc   1140

cgggccttca tcgccgagga ggggtggcta ttggtggccc tggactatag ccagatagag   1200

ctcagggtgc tggcccacct ctccggcgac gagaacctga tccgggtctt ccaggagggg   1260

cgggacatcc acacggagac cgccagctgg atgttcggcg tcccccggga ggccgtggac   1320

cccctgatgc gccgggcggc caagaccatc aactacgggg tcctctacgg catgtcggcc   1380

caccgcctct cccaggagct agccatccct tacgaggagg cccaggcctt cattgagcgc   1440

tactttcaga gcttccccaa ggtgcgggcc tggattgaga agaccctgga ggagggcagg   1500

aggcgggggt acgtggagac cctcttcggc cgccgccgct acgtgccaga cctagaggcc   1560

cgggtgaaga gcgtgcggga ggcggccgag cgcatggcct tcaacatgcc cgtccagggc   1620

accgccgccg acctcatgaa gctggctatg gtgaagctct tccccaggct ggaggaaatg   1680

ggggccagga tgctccttca ggtccacgac gagctggtcc tcgaggcccc aaaagagagg   1740

gcggaggccg tggcccggct ggccaaggag gtcatggagg gggtgtatcc cctggccgtg   1800

cccctggagg tggaggtggg gataggggag gactggctct ccgccaagga gggcattgat   1860

ggccgcggcg gaggcgggca tcatcatcat catcattaa                          1899
```

```
<210> SEQ ID NO 31
<211> LENGTH: 632
<212> TYPE: PRT
<213> ORGANISM: Artificial Sequence
<220> FEATURE:
<223> OTHER INFORMATION: Description of Artificial
      Sequence:Sso7d-deltaTaq(Y) fusion protein

<400> SEQUENCE: 31

Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Trp Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Gly Val Thr Ser Pro Lys Ala Leu Glu
 65                  70                  75                  80

Glu Ala Pro Trp Pro Pro Pro Glu Gly Ala Phe Val Gly Phe Val Leu
                 85                  90                  95

Ser Arg Lys Glu Pro Met Trp Ala Asp Leu Leu Ala Leu Ala Ala Ala
            100                 105                 110
```

-continued

```
Arg Gly Gly Arg Val His Arg Ala Pro Glu Pro Tyr Lys Ala Leu Arg
        115                 120                 125

Asp Leu Lys Glu Ala Arg Gly Leu Leu Ala Lys Asp Leu Ser Val Leu
    130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
            180                 185                 190

Leu Ser Glu Arg Leu Phe Ala Asn Leu Trp Gly Arg Leu Glu Gly Glu
        195                 200                 205

Glu Arg Leu Leu Trp Leu Tyr Arg Glu Val Glu Arg Pro Leu Ser Ala
    210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
            260                 265                 270

Asp Gln Leu Glu Arg Val Leu Phe Asp Glu Leu Gly Leu Pro Ala Ile
        275                 280                 285

Gly Lys Thr Glu Lys Thr Gly Lys Arg Ser Thr Ser Ala Ala Val Leu
    290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
            340                 345                 350

Ala Thr Ala Thr Gly Arg Leu Ser Ser Ser Asp Pro Asn Leu Gln Asn
        355                 360                 365

Ile Pro Val Arg Thr Pro Leu Gly Gln Arg Ile Arg Arg Ala Phe Ile
    370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415

Phe Gln Glu Gly Arg Asp Ile His Thr Glu Thr Ala Ser Trp Met Phe
            420                 425                 430

Gly Val Pro Arg Glu Ala Val Asp Pro Leu Met Arg Arg Ala Ala Lys
        435                 440                 445

Thr Ile Asn Tyr Gly Val Leu Tyr Gly Met Ser Ala His Arg Leu Ser
    450                 455                 460

Gln Glu Leu Ala Ile Pro Tyr Glu Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Arg Gly Tyr Val Glu Thr Leu Phe Gly Arg Arg
            500                 505                 510

Arg Tyr Val Pro Asp Leu Glu Ala Arg Val Lys Ser Val Arg Glu Ala
        515                 520                 525

Ala Glu Arg Met Ala Phe Asn Met Pro Val Gln Gly Thr Ala Ala Asp
```

-continued

```
    530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
            580                 585                 590

Glu Gly Val Tyr Pro Leu Ala Val Pro Leu Glu Val Glu Val Gly Ile
        595                 600                 605

Gly Glu Asp Trp Leu Ser Ala Lys Glu Gly Ile Asp Gly Arg Gly Gly
    610                 615                 620

Gly Gly His His His His His His
625                 630


<210> SEQ ID NO 32
<211> LENGTH: 2763
<212> TYPE: DNA
<213> ORGANISM: Artificial Sequence
<220> FEATURE:
<223> OTHER INFORMATION: Description of Artificial Sequence:Sso7d-
      deltaTaq (E5)(Y) fusion protein

<400> SEQUENCE: 32

atgattacga attcgagcgc aaccgtaaag ttcaagtaca aaggcgaaga aaaagaggta     60

gacatctcca agatcaagaa agtatggcgt gtgggcaaga tgatctcctt cacctacgac    120

gagggcggtg gcaagaccgg ccgtggtgcg gtaagcgaaa aggacgcgcc gaaggagctg    180

ctgcagatgc tggagaagca gaaaaagggc ggcggtgtca ctagtgggat gctgcccctc    240

tttgagccca agggccgggt cctcctggtg gacggccacc acctggccta ccgcaccttc    300

cacgccctga agggcctcac caccagccgg ggggagccgg tgcaggcggt ctacggcttc    360

gccaagagcc tcctcaaggc cctcaaggag gacggggacg cggtgatcgt ggtctttgac    420

gccaaggccc cctccttccc ccacgaggcc tacgggggc acaaggcggg ccgggccccc    480

acgccagagg actttccccg gcaactcgcc ctcatcaagg agctggtgga cctcctgggg    540

ctggcgcgcc tcgaggtccc gggctacgag gcggacgacg tcctggccag cctggccaag    600

aaggcggaaa aggagggcta cgaggtccgc atcctcaccg ccgacaaaga cctttaccag    660

ctcctttccg accgcatcca cgtcctccac cccgaggggt acctcatcac cccggcctgg    720

ctttgggaaa agtacggcct gaggcccgac cagtgggccg actaccgggc cctgaccggg    780

gacgagtccg acaaccttcc cggggtcaag ggcatcgggg agaagacggc gaggaagctt    840

ctggaggagt gggggagcct ggaagccctc ctcaagaacc tggaccggct gaagcccgcc    900

atccgggaga agatcctggc ccacatggac gatctgaagc tctcctggga cctggccaag    960

gtgcgcaccg acctgcccct ggaggtggac ttcgccaaaa ggcgggagcc cgaccgggag   1020

aggcttaggg cctttctgga gaggcttgag tttggcagcc tcctccacga gttcggcctt   1080

ctggaaagcc ccaaggccct ggaggaggcc ccctggcccc cgccggaagg ggccttcgtg   1140

ggctttgtgc tttcccgcaa ggagcccatg tgggccgatc ttctggccct ggccgccgcc   1200

aggggggggcc gggtccaccg ggcccccgag ccttataaag ccctcaggga cctgaaggag   1260

gcgcgggggc ttctcgccaa agacctgagc gttctggccc tgagggaagg ccttggcctc   1320

ccgcccggcg acgaccccat gctcctcgcc tacctcctgg acccttccaa caccaccccc   1380

gagggggtgg cccggcgcta cggcggggag tggacggagg aggcggggga gcgggccgcc   1440
```

```
ctttccgaga ggctcttcgc caacctgtgg gggaggcttg agggggagga gaggctcctt   1500

tggctttacc gggaggtgga gaggcccctt tccgctgtcc tggcccacat ggaggccacg   1560

ggggtgcgcc tggacgtggc ctatctcagg gccttgtccc tggaggtggc cgaggagatc   1620

gcccgcctcg aggccgaggt cttccgcctg gccggccacc ccttcaacct caactcccgg   1680

gaccagctgg aaagggtcct ctttgacgag ctagggcttc ccgccatcgg caagacggag   1740

aagaccggca agcgctccac cagcgccgcc gtcctggagg ccctccgcga ggcccacccc   1800

atcgtggaga agatcctgca gtaccgggag ctcaccaagc tgaagagcac ctacattgac   1860

cccttgccgg acctcatcca ccccaggacg ggccgcctcc acacccgctt caaccagacg   1920

gccacggcca cgggcaggct aagtagctcc gatcccaacc tccagaacat ccccgtccgc   1980

accccgcttg ggcagaggat ccgccgggcc ttcatcgccg aggaggggtg gctattggtg   2040

gccctggact atagccagat agagctcagg gtgctggccc acctctccgg cgacgagaac   2100

ctgatccggg tcttccagga ggggcgggac atccacacgg agaccgccag ctggatgttc   2160

ggcgtccccc gggaggccgt ggacccccctg atgcgccggg cggccaagac catcaactac   2220

ggggtcctct acggcatgtc ggcccaccgc ctctcccagg agctagccat cccttacgag   2280

gaggcccagg ccttcattga gcgctacttt cagagcttcc ccaaggtgcg ggcctggatt   2340

gagaagaccc tggaggaggg caggaggcgg gggtacgtgg agaccctctt cggccgccgc   2400

cgctacgtgc cagacctaga ggcccgggtg aagagcgtgc gggaggcggc cgagcgcatg   2460

gccttcaaca tgcccgtcca gggcaccgcc gccgacctca tgaagctggc tatggtgaag   2520

ctcttcccca ggctggagga aatgggggcc aggatgctcc ttcaggtcca cgacgagctg   2580

gtcctcgagg ccccaaaaga gagggcggag gccgtggccc ggctggccaa ggaggtcatg   2640

gagggggtgt atcccctggc cgtgcccctg gaggtggagg tggggatagg ggaggactgg   2700

ctctccgcca aggagggcat tgatggccgc ggcggaggcg ggcatcatca tcatcatcat   2760

taa                                                                2763
```

<210> SEQ ID NO 33
<211> LENGTH: 920
<212> TYPE: PRT
<213> ORGANISM: Artificial Sequence
<220> FEATURE:
<223> OTHER INFORMATION: Description of Artificial Sequence:Sso7d-deltaTaq (E5)(Y) fusion protein

<400> SEQUENCE: 33

```
Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Trp Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Gly Val Thr Ser Gly Met Leu Pro Leu
 65                  70                  75                  80

Phe Glu Pro Lys Gly Arg Val Leu Leu Val Asp Gly His His Leu Ala
                 85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
```

-continued

```
        115                 120                 125

Lys Glu Asp Gly Asp Ala Val Ile Val Val Phe Asp Ala Lys Ala Pro
    130                 135                 140

Ser Phe Pro His Glu Ala Tyr Gly Gly His Lys Ala Gly Arg Ala Pro
145                 150                 155                 160

Thr Pro Glu Asp Phe Pro Arg Gln Leu Ala Leu Ile Lys Glu Leu Val
                165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
        195                 200                 205

Val Arg Ile Leu Thr Ala Asp Lys Asp Leu Tyr Gln Leu Leu Ser Asp
    210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
                245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
        275                 280                 285

Ala Leu Leu Lys Asn Leu Asp Arg Leu Lys Pro Ala Ile Arg Glu Lys
    290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
                325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
        355                 360                 365

Glu Ala Pro Trp Pro Pro Pro Glu Gly Ala Phe Val Gly Phe Val Leu
    370                 375                 380

Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
                405                 410                 415

Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
        435                 440                 445

Leu Ala Tyr Leu Leu Asp Pro Ser Asn Thr Thr Pro Glu Gly Val Ala
    450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu
                485                 490                 495

Glu Arg Leu Leu Trp Leu Tyr Arg Glu Val Glu Arg Pro Leu Ser Ala
            500                 505                 510

Val Leu Ala His Met Glu Ala Thr Gly Val Arg Leu Asp Val Ala Tyr
        515                 520                 525

Leu Arg Ala Leu Ser Leu Glu Val Ala Glu Glu Ile Ala Arg Leu Glu
    530                 535                 540
```

```
Ala Glu Val Phe Arg Leu Ala Gly His Pro Phe Asn Leu Asn Ser Arg
545                 550                 555                 560

Asp Gln Leu Glu Arg Val Leu Phe Asp Glu Leu Gly Leu Pro Ala Ile
                565                 570                 575

Gly Lys Thr Glu Lys Thr Gly Lys Arg Ser Thr Ser Ala Ala Val Leu
            580                 585                 590

Glu Ala Leu Arg Glu Ala His Pro Ile Val Glu Lys Ile Leu Gln Tyr
        595                 600                 605

Arg Glu Leu Thr Lys Leu Lys Ser Thr Tyr Ile Asp Pro Leu Pro Asp
    610                 615                 620

Leu Ile His Pro Arg Thr Gly Arg Leu His Thr Arg Phe Asn Gln Thr
625                 630                 635                 640

Ala Thr Ala Thr Gly Arg Leu Ser Ser Ser Asp Pro Asn Leu Gln Asn
                645                 650                 655

Ile Pro Val Arg Thr Pro Leu Gly Gln Arg Ile Arg Arg Ala Phe Ile
            660                 665                 670

Ala Glu Glu Gly Trp Leu Leu Val Ala Leu Asp Tyr Ser Gln Ile Glu
        675                 680                 685

Leu Arg Val Leu Ala His Leu Ser Gly Asp Glu Asn Leu Ile Arg Val
    690                 695                 700

Phe Gln Glu Gly Arg Asp Ile His Thr Glu Thr Ala Ser Trp Met Phe
705                 710                 715                 720

Gly Val Pro Arg Glu Ala Val Asp Pro Leu Met Arg Arg Ala Ala Lys
                725                 730                 735

Thr Ile Asn Tyr Gly Val Leu Tyr Gly Met Ser Ala His Arg Leu Ser
            740                 745                 750

Gln Glu Leu Ala Ile Pro Tyr Glu Glu Ala Gln Ala Phe Ile Glu Arg
        755                 760                 765

Tyr Phe Gln Ser Phe Pro Lys Val Arg Ala Trp Ile Glu Lys Thr Leu
    770                 775                 780

Glu Glu Gly Arg Arg Arg Gly Tyr Val Glu Thr Leu Phe Gly Arg Arg
785                 790                 795                 800

Arg Tyr Val Pro Asp Leu Glu Ala Arg Val Lys Ser Val Arg Glu Ala
                805                 810                 815

Ala Glu Arg Met Ala Phe Asn Met Pro Val Gln Gly Thr Ala Ala Asp
            820                 825                 830

Leu Met Lys Leu Ala Met Val Lys Leu Phe Pro Arg Leu Glu Glu Met
        835                 840                 845

Gly Ala Arg Met Leu Leu Gln Val His Asp Glu Leu Val Leu Glu Ala
    850                 855                 860

Pro Lys Glu Arg Ala Glu Ala Val Ala Arg Leu Ala Lys Glu Val Met
865                 870                 875                 880

Glu Gly Val Tyr Pro Leu Ala Val Pro Leu Glu Val Glu Val Gly Ile
                885                 890                 895

Gly Glu Asp Trp Leu Ser Ala Lys Glu Gly Ile Asp Gly Arg Gly Gly
            900                 905                 910

Gly Gly His His His His His His
        915                 920
```

<210> SEQ ID NO 34
<211> LENGTH: 4
<212> TYPE: PRT
<213> ORGANISM: Artificial Sequence
<220> FEATURE:

-continued

```
<223> OTHER INFORMATION: Description of Artificial Sequence:peptide
      linker

<400> SEQUENCE: 34

Gly Gly Val Thr
  1


<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:peptide
 linker

<400> SEQUENCE: 35

Gly Thr Gly Gly Gly Gly
  1               5


<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence:lysine-rich
      peptide

<400> SEQUENCE: 36

Asn Ser Lys Lys Lys Lys Lys Lys Lys Arg Lys Lys Arg Lys Lys Lys
  1               5                  10                  15

Gly Gly Gly Val Thr
            20
```